(12) United States Patent
Levinson

(10) Patent No.: US 8,676,338 B2
(45) Date of Patent: Mar. 18, 2014

(54) COMBINED MODALITY TREATMENT SYSTEMS, METHODS AND APPARATUS FOR BODY CONTOURING APPLICATIONS

(75) Inventor: Mitchell E. Levinson, Pleasanton, CA (US)

(73) Assignee: Zeltiq Aesthetics, Inc., Pleasanton, CA (US)

( * ) Notice: Subject to any disclaimer, the term of this patent is extended or adjusted under 35 U.S.C. 154(b) by 465 days.

(21) Appl. No.: 12/840,235

(22) Filed: Jul. 20, 2010

(65) Prior Publication Data

US 2012/0022518 A1 Jan. 26, 2012

(51) Int. Cl.
*A61F 7/00* (2006.01)

(52) U.S. Cl.
USPC ............................................ 607/101; 607/96

(58) Field of Classification Search
USPC .................................................. 607/101, 96
See application file for complete search history.

(56) References Cited

U.S. PATENT DOCUMENTS

| | | |
|---|---|---|
| 681,806 A | 9/1901 | Mignault |
| 889,810 A | 6/1908 | Robinson |
| 2,516,491 A | 7/1950 | Swastek |
| 2,766,619 A | 10/1956 | Tribus et al. |
| 3,093,135 A | 6/1963 | Hirschhorn |
| 3,132,688 A | 5/1964 | Nowak |
| 3,282,267 A | 11/1966 | Wiliam |
| 3,502,080 A | 3/1970 | Hirschhorn |
| 3,587,577 A | 6/1971 | Smirnov et al. |
| 3,591,645 A | 7/1971 | Selwitz |
| 3,703,897 A | 11/1972 | Mack et al. |
| 3,786,814 A | 1/1974 | Armao |
| 3,827,436 A | 8/1974 | Stumpf et al. |
| 3,942,519 A | 3/1976 | Shock |
| 3,948,269 A | 4/1976 | Zimmer |
| 3,986,385 A | 10/1976 | Johnston et al. |
| 4,002,221 A | 1/1977 | Buchalter |

(Continued)

FOREIGN PATENT DOCUMENTS

| | | |
|---|---|---|
| CN | 1511503 | 7/2004 |
| CN | 1741777 A | 3/2006 |

(Continued)

OTHER PUBLICATIONS

European Search Report, European Patent Application No. 10167756.5, Applicant: The General Hospital Corporation, Mailing Dates: Aug. 31, 2010, 6 pages.

(Continued)

*Primary Examiner* — Linda Dvorak
*Assistant Examiner* — Kaitlyn Smith
(74) *Attorney, Agent, or Firm* — Perkins Coie LLP

(57) ABSTRACT

Systems and methods that enable delivery of radiofrequency energy and cryotherapy applications to adipose tissue for reduction and contouring of body fat are described herein. Aspects of the disclosure are directed to methods for reducing surface irregularities in a surface of a subject's skin resulting from an uneven distribution of adipose tissue in the subcutaneous layer. The method can include delivering capacitively coupled or conductively coupled radiofrequency energy to a target region of the subject at a frequency which selectively heats fibrous septae in a subcutaneous layer of the target region to a maximum temperature less than a fibrous septae denaturation temperature. Furthermore, the method can include removing heat such that lipid-rich lobules in the subcutaneous layer are affected while non-lipid-rich cells and lipid-rich regions adjacent to the fibrous septae are not substantially affected.

30 Claims, 6 Drawing Sheets

(56) References Cited

U.S. PATENT DOCUMENTS

| | | |
|---|---|---|
| 4,140,130 A | 2/1979 | Storm, III |
| 4,178,429 A | 12/1979 | Scheffer |
| 4,202,336 A | 5/1980 | van Gerven et al. |
| 4,266,043 A | 5/1981 | Fujii et al. |
| 4,381,009 A | 4/1983 | Del Bon et al. |
| 4,483,341 A | 11/1984 | Witteles |
| 4,528,979 A | 7/1985 | Marchenko et al. |
| 4,531,524 A | 7/1985 | Mioduski |
| 4,548,212 A | 10/1985 | Leung |
| 4,555,313 A | 11/1985 | Duchane et al. |
| 4,585,002 A | 4/1986 | Kissin |
| 4,603,076 A | 7/1986 | Bowditch et al. |
| 4,614,191 A | 9/1986 | Perler |
| 4,644,955 A | 2/1987 | Mioduski |
| 4,664,110 A | 5/1987 | Schanzlin |
| 4,700,701 A | 10/1987 | Montaldi |
| 4,718,429 A | 1/1988 | Smidt |
| 4,741,338 A | 5/1988 | Miyamae et al. |
| 4,764,463 A | 8/1988 | Mason et al. |
| 4,802,475 A | 2/1989 | Weshahy et al. |
| 4,832,022 A | 5/1989 | Tjulkov et al. |
| 4,846,176 A | 7/1989 | Golden |
| 4,869,250 A | 9/1989 | Bitterly |
| 4,880,564 A | 11/1989 | Abel et al. |
| 4,906,463 A | 3/1990 | Cleary et al. |
| 4,930,317 A | 6/1990 | Klein |
| 4,935,345 A | 6/1990 | Guilbeau et al. |
| 4,961,422 A | 10/1990 | Marchosky et al. |
| 4,962,761 A | 10/1990 | Golden |
| 4,990,144 A | 2/1991 | Blott |
| 5,007,433 A | 4/1991 | Hermsdorffer et al. |
| 5,018,521 A | 5/1991 | Campbell |
| 5,065,752 A | 11/1991 | Sessions et al. |
| 5,069,208 A | 12/1991 | Noppel et al. |
| 5,084,671 A | 1/1992 | Miyata et al. |
| 5,108,390 A | 4/1992 | Potocky et al. |
| 5,119,674 A | 6/1992 | Nielsen et al. |
| 5,143,063 A | 9/1992 | Fellner |
| 5,148,804 A | 9/1992 | Hill et al. |
| 5,169,384 A | 12/1992 | Bosniak et al. |
| 5,197,466 A | 3/1993 | Marchosky et al. |
| 5,207,674 A | 5/1993 | Hamilton |
| 5,221,726 A | 6/1993 | Dabi et al. |
| 5,264,234 A | 11/1993 | Windhab et al. |
| 5,277,030 A | 1/1994 | Miller |
| 5,314,423 A | 5/1994 | Seney |
| 5,330,745 A | 7/1994 | McDow |
| 5,336,616 A | 8/1994 | Livesey et al. |
| 5,339,541 A | 8/1994 | Owens |
| 5,351,677 A | 10/1994 | Kami et al. |
| 5,362,966 A | 11/1994 | Rosenthal et al. |
| 5,363,347 A | 11/1994 | Nguyen |
| 5,427,772 A | 6/1995 | Hagan |
| 5,433,717 A | 7/1995 | Rubinsky et al. |
| 5,456,703 A | 10/1995 | Beeuwkes, III |
| 5,472,416 A | 12/1995 | Blugerman et al. |
| 5,497,596 A | 3/1996 | Zatkulak |
| 5,505,726 A | 4/1996 | Meserol |
| 5,505,730 A | 4/1996 | Edwards |
| 5,507,790 A | 4/1996 | Weiss et al. |
| 5,514,105 A | 5/1996 | Goodman, Jr. et al. |
| 5,514,170 A | 5/1996 | Mauch |
| 5,531,742 A | 7/1996 | Barken |
| 5,562,604 A | 10/1996 | Yablon et al. |
| 5,571,801 A | 11/1996 | Segall et al. |
| 5,603,221 A | 2/1997 | Maytal |
| 5,628,769 A | 5/1997 | Saringer et al. |
| 5,647,868 A | 7/1997 | Chinn |
| 5,650,450 A | 7/1997 | Lovette et al. |
| 5,651,773 A | 7/1997 | Perry et al. |
| 5,654,279 A | 8/1997 | Rubinsky et al. |
| 5,654,546 A | 8/1997 | Lindsay |
| 5,660,836 A * | 8/1997 | Knowlton ............ 424/400 |
| 5,672,172 A | 9/1997 | Zupkas |
| 5,733,280 A | 3/1998 | Avitall |
| 5,741,248 A | 4/1998 | Stern et al. |
| 5,746,736 A | 5/1998 | Tankovich |
| 5,755,663 A | 5/1998 | Larsen et al. |
| 5,755,753 A | 5/1998 | Knowlton |
| 5,759,182 A | 6/1998 | Varney et al. |
| 5,759,764 A | 6/1998 | Polovina |
| 5,769,879 A | 6/1998 | Richards et al. |
| 5,817,050 A | 10/1998 | Klein |
| 5,830,208 A | 11/1998 | Muller |
| 5,833,685 A | 11/1998 | Tortal et al. |
| 5,844,013 A | 12/1998 | Kenndoff et al. |
| 5,871,524 A | 2/1999 | Knowlton |
| 5,871,526 A | 2/1999 | Gibbs et al. |
| 5,895,418 A | 4/1999 | Saringer et al. |
| 5,901,707 A | 5/1999 | Gonçalves et al. |
| 5,919,219 A | 7/1999 | Knowlton |
| 5,944,748 A | 8/1999 | Mager et al. |
| 5,948,011 A * | 9/1999 | Knowlton ............ 607/101 |
| 5,964,092 A | 10/1999 | Tozuka et al. |
| 5,964,749 A | 10/1999 | Eckhouse et al. |
| 5,967,976 A | 10/1999 | Larsen et al. |
| 5,986,167 A | 11/1999 | Arteman et al. |
| 6,017,337 A | 1/2000 | Pira et al. |
| 6,023,932 A | 2/2000 | Johnston et al. |
| 6,032,675 A | 3/2000 | Rubinsky |
| 6,039,694 A | 3/2000 | Larson et al. |
| 6,041,787 A | 3/2000 | Rubinsky |
| 6,051,159 A | 4/2000 | Hao et al. |
| 6,074,415 A | 6/2000 | Der Ovanesian |
| 6,093,230 A | 7/2000 | Johnson, III et al. |
| 6,102,885 A | 8/2000 | Bass |
| 6,120,519 A | 9/2000 | Weber et al. |
| 6,150,148 A | 11/2000 | Nanda et al. |
| 6,180,867 B1 | 1/2001 | Hedengren et al. |
| 6,241,753 B1 | 6/2001 | Knowlton |
| 6,264,649 B1 | 7/2001 | Whitcroft et al. |
| 6,273,884 B1 | 8/2001 | Altshuler et al. |
| 6,290,988 B1 | 9/2001 | Van Vilsteren et al. |
| 6,311,090 B1 | 10/2001 | Knowlton |
| 6,311,497 B1 | 11/2001 | Chung |
| 6,350,276 B1 | 2/2002 | Knowlton |
| 6,354,297 B1 | 3/2002 | Eiseman |
| 6,377,854 B1 * | 4/2002 | Knowlton ............ 607/101 |
| 6,377,855 B1 | 4/2002 | Knowlton |
| 6,381,497 B1 | 4/2002 | Knowlton |
| 6,381,498 B1 | 4/2002 | Knowlton |
| 6,387,380 B1 * | 5/2002 | Knowlton ............ 424/400 |
| 6,405,090 B1 | 6/2002 | Knowlton |
| 6,413,255 B1 | 7/2002 | Stern |
| 6,425,912 B1 | 7/2002 | Knowlton |
| 6,426,445 B1 | 7/2002 | Young et al. |
| 6,430,446 B1 | 8/2002 | Knowlton |
| 6,430,956 B1 | 8/2002 | Haas et al. |
| 6,438,424 B1 | 8/2002 | Knowlton |
| 6,438,954 B1 | 8/2002 | Goetz et al. |
| 6,438,964 B1 | 8/2002 | Giblin |
| 6,453,202 B1 | 9/2002 | Knowlton |
| 6,461,378 B1 | 10/2002 | Knowlton |
| 6,470,216 B1 | 10/2002 | Knowlton |
| 6,471,693 B1 | 10/2002 | Carroll et al. |
| 6,494,844 B1 | 12/2002 | Van Bladel et al. |
| 6,519,964 B2 | 2/2003 | Bieberich |
| 6,523,354 B1 | 2/2003 | Tolbert |
| 6,527,765 B2 | 3/2003 | Kelman et al. |
| 6,544,248 B1 | 4/2003 | Bass |
| 6,548,297 B1 | 4/2003 | Kuri-Harcuch et al. |
| 6,551,255 B2 | 4/2003 | Van Bladel et al. |
| 6,551,348 B1 | 4/2003 | Blalock et al. |
| 6,551,349 B2 | 4/2003 | Lasheras et al. |
| 6,569,189 B1 | 5/2003 | Augustine et al. |
| 6,592,577 B2 | 7/2003 | Abboud et al. |
| 6,605,080 B1 | 8/2003 | Altshuler et al. |
| 6,626,854 B2 | 9/2003 | Friedman et al. |
| 6,635,053 B1 | 10/2003 | Lalonde et al. |
| 6,645,162 B2 | 11/2003 | Friedman et al. |
| 6,645,229 B2 | 11/2003 | Matsumura et al. |
| 6,648,904 B2 | 11/2003 | Altshuler et al. |
| 6,697,670 B2 | 2/2004 | Chomenky et al. |
| 6,699,266 B2 | 3/2004 | Lachenbruch et al. |

(56) References Cited

U.S. PATENT DOCUMENTS

| | | | |
|---|---|---|---|
| 6,718,785 B2 | 4/2004 | Bieberich |
| 6,746,474 B2 | 6/2004 | Saadat |
| 6,749,624 B2 | 6/2004 | Knowlton |
| 6,764,502 B2 | 7/2004 | Bieberich |
| 6,789,545 B2 | 9/2004 | Littrup et al. |
| 6,795,728 B2 | 9/2004 | Chornenky et al. |
| 6,820,961 B2 | 11/2004 | Johnson |
| 6,821,274 B2 | 11/2004 | McHale et al. |
| 6,840,955 B2 | 1/2005 | Ein |
| 6,878,144 B2 | 4/2005 | Altshuler et al. |
| 6,904,956 B2 | 6/2005 | Noel |
| 6,918,903 B2 | 7/2005 | Bass |
| 6,942,022 B2 | 9/2005 | Blangetti et al. |
| 6,945,942 B2 | 9/2005 | Van Bladel et al. |
| 6,948,903 B2 | 9/2005 | Ablabutyan et al. |
| 7,005,558 B1 | 2/2006 | Johansson et al. |
| 7,006,874 B2 | 2/2006 | Knowlton et al. |
| 7,022,121 B2 | 4/2006 | Stern et al. |
| 7,037,326 B2 | 5/2006 | Lee et al. |
| 7,077,858 B2 | 7/2006 | Fletcher et al. |
| 7,081,111 B2 | 7/2006 | Svaasand et al. |
| 7,083,612 B2 | 8/2006 | Littrup et al. |
| 7,096,204 B1 | 8/2006 | Chen et al. |
| 7,112,712 B1 | 9/2006 | Ancell |
| 7,115,123 B2 | 10/2006 | Knowlton et al. |
| 7,141,049 B2 | 11/2006 | Stern et al. |
| 7,183,360 B2 | 2/2007 | Daniel et al. |
| 7,189,252 B2 | 3/2007 | Krueger |
| 7,192,426 B2 | 3/2007 | Baust et al. |
| 7,204,832 B2 | 4/2007 | Altshuler et al. |
| 7,220,778 B2 | 5/2007 | Anderson et al. |
| 7,229,436 B2 | 6/2007 | Stern et al. |
| 7,258,674 B2 | 8/2007 | Cribbs et al. |
| 7,267,675 B2 | 9/2007 | Stern et al. |
| 7,347,855 B2 | 3/2008 | Eshel et al. |
| 7,367,341 B2 | 5/2008 | Anderson et al. |
| 7,713,266 B2 | 5/2010 | Elkins et al. |
| 7,854,754 B2 | 12/2010 | Ting et al. |
| RE42,277 E | 4/2011 | Chornenky et al. |
| 7,938,824 B2 | 5/2011 | Chornenky et al. |
| RE42,835 E | 10/2011 | Chornenky et al. |
| RE43,009 E | 12/2011 | Chornenky et al. |
| 8,133,191 B2 | 3/2012 | Rosenberg et al. |
| 8,192,474 B2 | 6/2012 | Levinson |
| 8,275,442 B2 | 9/2012 | Allison |
| 8,337,539 B2 | 12/2012 | Ting et al. |
| 2001/0031459 A1 | 10/2001 | Fahy et al. |
| 2001/0039439 A1 | 11/2001 | Elkins et al. |
| 2002/0049483 A1 | 4/2002 | Knowlton |
| 2002/0058975 A1 | 5/2002 | Bieberich |
| 2002/0062142 A1 | 5/2002 | Knowlton |
| 2002/0068338 A1 | 6/2002 | Nanda et al. |
| 2002/0117293 A1 | 8/2002 | Campbell |
| 2002/0120315 A1 | 8/2002 | Furuno et al. |
| 2002/0151887 A1 | 10/2002 | Stern et al. |
| 2002/0188286 A1 | 12/2002 | Quijano et al. |
| 2003/0044764 A1 | 3/2003 | Soane et al. |
| 2003/0055414 A1 | 3/2003 | Altshuler et al. |
| 2003/0069618 A1 | 4/2003 | Smith et al. |
| 2003/0077329 A1 | 4/2003 | Kipp et al. |
| 2003/0079488 A1 | 5/2003 | Bieberich |
| 2003/0100936 A1 | 5/2003 | Altshuler et al. |
| 2003/0109908 A1 | 6/2003 | Lachenbruch et al. |
| 2003/0109910 A1 | 6/2003 | Lachenbruch et al. |
| 2003/0125649 A1 | 7/2003 | McIntosh et al. |
| 2003/0199226 A1 | 10/2003 | Sommer et al. |
| 2003/0220635 A1 | 11/2003 | Knowlton et al. |
| 2003/0220674 A1 | 11/2003 | Anderson et al. |
| 2003/0236487 A1 | 12/2003 | Knowlton |
| 2004/0002705 A1 | 1/2004 | Knowlton et al. |
| 2004/0006328 A1 | 1/2004 | Anderson |
| 2004/0009936 A1 | 1/2004 | Tang et al. |
| 2004/0030332 A1 | 2/2004 | Knowlton et al. |
| 2004/0034341 A1 | 2/2004 | Altshuler et al. |
| 2004/0039312 A1 | 2/2004 | Hillstead et al. |
| 2004/0044384 A1 | 3/2004 | Leber et al. |
| 2004/0049178 A1 | 3/2004 | Abboud et al. |
| 2004/0073079 A1 | 4/2004 | Altshuler et al. |
| 2004/0074629 A1 | 4/2004 | Noel |
| 2004/0093042 A1 | 5/2004 | Altshuler et al. |
| 2004/0104012 A1 | 6/2004 | Zhou et al. |
| 2004/0162596 A1 | 8/2004 | Altshuler et al. |
| 2004/0176667 A1 | 9/2004 | Mihai et al. |
| 2004/0199226 A1 | 10/2004 | Shadduck |
| 2004/0206365 A1* | 10/2004 | Knowlton ............... 128/898 |
| 2004/0210214 A1 | 10/2004 | Knowlton |
| 2004/0210287 A1 | 10/2004 | Greene |
| 2004/0215294 A1 | 10/2004 | Littrup et al. |
| 2004/0259855 A1 | 12/2004 | Anderson et al. |
| 2005/0049661 A1 | 3/2005 | Koffroth |
| 2005/0143781 A1 | 6/2005 | Carbunaru et al. |
| 2005/0154431 A1 | 7/2005 | Quistgaard et al. |
| 2005/0159986 A1 | 7/2005 | Breeland et al. |
| 2005/0182462 A1 | 8/2005 | Chornenky et al. |
| 2005/0187597 A1 | 8/2005 | Vanderschuit |
| 2005/0222565 A1 | 10/2005 | Manstein |
| 2005/0251120 A1 | 11/2005 | Anderson et al. |
| 2005/0261753 A1 | 11/2005 | Littrup et al. |
| 2005/0283144 A1 | 12/2005 | Shiono et al. |
| 2006/0030778 A1 | 2/2006 | Mendlein et al. |
| 2006/0036300 A1 | 2/2006 | Kreindel |
| 2006/0041704 A1 | 2/2006 | Choi |
| 2006/0074313 A1 | 4/2006 | Slayton et al. |
| 2006/0079852 A1 | 4/2006 | Bubb et al. |
| 2006/0122509 A1 | 6/2006 | Desilets |
| 2006/0200063 A1 | 9/2006 | Munro et al. |
| 2006/0206110 A1 | 9/2006 | Knowlton et al. |
| 2006/0234899 A1 | 10/2006 | Nekmard et al. |
| 2006/0265032 A1* | 11/2006 | Hennings et al. ............. 607/89 |
| 2006/0270745 A1 | 11/2006 | Hunt et al. |
| 2007/0010811 A1 | 1/2007 | Stern et al. |
| 2007/0010861 A1 | 1/2007 | Anderson et al. |
| 2007/0032561 A1 | 2/2007 | Lin et al. |
| 2007/0055173 A1 | 3/2007 | DeLonzor et al. |
| 2007/0078502 A1 | 4/2007 | Weber et al. |
| 2007/0106342 A1 | 5/2007 | Schumann |
| 2007/0129714 A1 | 6/2007 | Elkins et al. |
| 2007/0141265 A1 | 6/2007 | Thomson |
| 2007/0198071 A1 | 8/2007 | Ting et al. |
| 2007/0239075 A1 | 10/2007 | Rosenberg et al. |
| 2007/0249519 A1 | 10/2007 | Guha et al. |
| 2007/0255274 A1 | 11/2007 | Stern et al. |
| 2007/0255362 A1* | 11/2007 | Levinson et al. ............. 607/96 |
| 2007/0265614 A1 | 11/2007 | Stern et al. |
| 2007/0270925 A1 | 11/2007 | Levinson |
| 2007/0282249 A1 | 12/2007 | Quisenberry et al. |
| 2007/0282318 A1* | 12/2007 | Spooner et al. ............. 606/32 |
| 2008/0077201 A1* | 3/2008 | Levinson et al. ............. 607/96 |
| 2008/0077202 A1 | 3/2008 | Levinson |
| 2008/0077211 A1* | 3/2008 | Levinson et al. ............ 607/108 |
| 2008/0140371 A1 | 6/2008 | Warner |
| 2008/0183164 A1 | 7/2008 | Elkins et al. |
| 2008/0287839 A1 | 11/2008 | Rosen et al. |
| 2009/0018623 A1* | 1/2009 | Levinson et al. ............. 607/96 |
| 2009/0018624 A1* | 1/2009 | Levinson et al. ............. 607/96 |
| 2009/0018625 A1* | 1/2009 | Levinson et al. ............. 607/96 |
| 2009/0018626 A1* | 1/2009 | Levinson et al. ............. 607/96 |
| 2009/0018627 A1* | 1/2009 | Levinson et al. ............. 607/96 |
| 2009/0118722 A1* | 5/2009 | Ebbers et al. ............. 606/21 |
| 2009/0149929 A1* | 6/2009 | Levinson et al. ............. 607/99 |
| 2009/0312676 A1 | 12/2009 | Rousso et al. |
| 2010/0028969 A1 | 2/2010 | Mueller et al. |
| 2010/0081971 A1 | 4/2010 | Allison |
| 2010/0152824 A1 | 6/2010 | Allison |
| 2010/0280582 A1 | 11/2010 | Baker et al. |
| 2011/0009860 A1 | 1/2011 | Chornenky et al. |
| 2011/0077723 A1 | 3/2011 | Parish et al. |
| 2011/0196438 A1 | 8/2011 | Mnozil et al. |
| 2012/0101549 A1 | 4/2012 | Schumann |
| 2012/0239123 A1 | 9/2012 | Weber et al. |
| 2013/0066309 A1 | 3/2013 | Levinson |
| 2013/0116758 A1 | 5/2013 | Levinson et al. |

(56) References Cited

U.S. PATENT DOCUMENTS

| | | | |
|---|---|---|---|
| 2013/0116759 A1 | 5/2013 | Levinson et al. | |
| 2013/0158440 A1 | 6/2013 | Allison | |
| 2013/0158636 A1 | 6/2013 | Ting et al. | |

FOREIGN PATENT DOCUMENTS

| | | | |
|---|---|---|---|
| CN | 1817990 A | 8/2006 | |
| DE | 532976 C | 9/1931 | |
| DE | 2851602 | 6/1980 | |
| DE | 4213584 A1 | 11/1992 | |
| DE | 4224595 | 1/1994 | |
| EP | 0263069 A2 | 4/1988 | |
| EP | 0397043 | 11/1990 | |
| EP | 0406244 A1 | 1/1991 | |
| EP | 0598824 A1 | 6/1994 | |
| EP | 1201266 | 5/2002 | |
| FR | 2745935 | 9/1997 | |
| GB | 2286660 A | 8/1995 | |
| GB | 2323659 A | 9/1998 | |
| JP | 63076895 A | 4/1988 | |
| JP | 03051964 A | 3/1991 | |
| JP | 3259975 A | 11/1991 | |
| JP | 4093597 A | 3/1992 | |
| JP | 6282977 A | 10/1994 | |
| JP | 7194666 | 8/1995 | |
| JP | 7194666 A | 8/1995 | |
| JP | 7268274 A | 10/1995 | |
| JP | 09164163 A | 6/1997 | |
| JP | 10216169 A | 8/1998 | |
| JP | 2000503154 A | 3/2000 | |
| JP | 3065657 | 7/2000 | |
| JP | 2002224051 | 8/2002 | |
| JP | 2002543668 A | 12/2002 | |
| JP | 2004013600 A | 1/2004 | |
| JP | 2004073812 | 11/2004 | |
| JP | 2005039790 A | 2/2005 | |
| JP | 3655820 | 3/2005 | |
| JP | 200565984 | 3/2005 | |
| JP | 2005110755 | 4/2005 | |
| JP | 2005520608 T | 7/2005 | |
| JP | 2008323716 | 11/2005 | |
| JP | 2006026001 A | 2/2006 | |
| JP | 2006520949 A | 9/2006 | |
| JP | 2008532591 | 8/2008 | |
| KR | 1020040094508 | 11/2004 | |
| TW | 0476644 | 2/2002 | |
| WO | WO-8503216 | 8/1985 | |
| WO | WO-94/04116 | 3/1994 | |
| WO | WO-9404116 | 3/1994 | |
| WO | WO-9636293 A1 | 11/1996 | |
| WO | WO-9637158 A1 | 11/1996 | |
| WO | WO-9705828 A1 | 2/1997 | |
| WO | WO-9722262 A2 | 6/1997 | |
| WO | WO-9725798 | 7/1997 | |
| WO | WO-9841156 A1 | 9/1998 | |
| WO | WO-9841157 A1 | 9/1998 | |
| WO | WO-9938469 A1 | 8/1999 | |
| WO | WO-0044346 A1 | 8/2000 | |
| WO | WO-00/65770 | 11/2000 | |
| WO | WO-0067685 | 11/2000 | |
| WO | WO-0114012 | 3/2001 | |
| WO | WO-0205736 A2 | 1/2002 | |
| WO | WO-02102921 A1 | 12/2002 | |
| WO | WO-0307859 A1 | 1/2003 | |
| WO | WO-03078596 A2 | 9/2003 | |
| WO | WO-04000098 A2 | 12/2003 | |
| WO | WO-2004080279 A2 | 9/2004 | |
| WO | WO-2004090939 | 10/2004 | |
| WO | WO-2005033957 | 4/2005 | |
| WO | WO-2005046540 A1 | 5/2005 | |
| WO | WO-2005096979 | 10/2005 | |
| WO | WO-2006/066226 | 6/2006 | |
| WO | WO-2006066226 A1 | 6/2006 | |
| WO | WO-2006094348 | 9/2006 | |
| WO | WO-2006106836 | 10/2006 | |
| WO | WO-2006127467 A2 | 11/2006 | |
| WO | WO-2007012083 | 1/2007 | |
| WO | WO-2007041642 A2 | 4/2007 | |
| WO | WO-2007127924 | 11/2007 | |
| WO | WO-2008039557 | 4/2008 | |
| WO | WO-2008143678 | 11/2008 | |
| WO | WO-2009/011708 | 1/2009 | |
| WO | WO-2009026471 | 2/2009 | |
| WO | WO-2010077841 A1 | 7/2010 | |
| WO | WO-2010127315 A2 | 11/2010 | |
| WO | WO-2012012296 | 1/2012 | |
| WO | WO-2012103242 | 8/2012 | |

OTHER PUBLICATIONS

Final Office Action; U.S. Appl. No. 11/528,225; Date of Mailing: Dec. 29, 2010, 12 pages.
Final Office Action; U.S. Appl. No. 11/558,046; Date of Mailing: Mar. 30, 2011, 17 pages.
International Search Report and Written Opinion for PCT/US2010/033290; Applicant: Zeltiq Aesthetics, Inc.; Mailed on Feb. 25, 2011, 12 pages.
International Search Report and Written Opinion for PCT/US2011/022112; Applicant: Zeltiq Aesthetics, Inc.; Mailed on Mar. 18, 2011, 11 pages.
International Search Report and Written Opinion for PCT/US2011/022444; Applicant: Zeltiq Aesthetics, Inc., Mailed on Mar. 29, 2011, 14 pages.
Non-Final Office Action; U.S. Appl. No. 12/942,852; Date of Mailing: Jun. 30, 2011, 10 pages.
Non-Final Office Action; U.S. Appl. No. 11/528,225; Date of Mailing: Aug. 3, 2011, 13 pages.
Non-Final Office Action; U.S. Appl. No. 12/565,613; Date of Mailing: Sep. 23, 2011, 55 pages.
Wang et al., "Cryopreservation of cell/hydrogel constructs based on a new cell-assembling technique", Sep. 5, 2009, 40 pages.
Wharton et al., "Cold acclimation and cryoprotectants in a freeze-tolerant Antarctic nematode, Panagrolaimus davidi," Mar. 7, 2000, 2 pages.
International Search Report and Written Opinion for PCT/US2011/044270; Applicant: Zeltiq Aesthetics, Inc.; Mailed on Nov. 21, 2011, 9 pages.
U.S. Appl. No. 12/275,002, filed Nov. 20, 2008, Martens.
U.S. Appl. No. 12/275,014, filed Nov. 20, 2008, Martens.
U.S. Appl. No. 12/772,040, filed Apr. 30, 2010, Baker et al.
Ardevol, "Cooling rates of tissue samples during freezing with liquid nitrogen," J. of Biochem and Biophysical Methods, 27, 77-86 (1993).
Bohm et al., "Saline-enhanced radiofrequency ablation of breast tissue: an in vitro feasibility study," Invest Radiol, 2000, pp. 149-157, vol. 35—issue (3).
Bondei, E. et al., "Disorders of Subcutaneous Tissue (Cold Panniculitis)," Dermatology in General Medicine, Chapter 108, Section 16: 1333-1334, 1993.
Burge, S.M. et al., "Hair Follicle Destruction and Regeneration in Guinea Pig Skin afer Cutaneous Freeze Injury," Cryobiology, 27(2): 153-163, 1990.
Coban, "Ischemia-Reperfusion Injury of Adipofascial Tissue: An Experimental Study Evaluating early Histologic and Biochemical Alterations in Rats," Mediators of Inflammation, 2005, 5, 304-308.
Donski et al., "The Effects of Cooling no Experimental Free Flap Survival," Brit J Plas Surg, 1980, pp. 353-360, vol. 33.
Duncan, W.C. et al., "Cold Panniculitis," Arch. Derm., 94:722-24, 1966.
Epstein, E.H. et al., "Popsicle Panniculitis," The New England Journal of Medicine, 282(17):996-67, 1970.
Final Office Action; U.S. Appl. No. 10/391,221; Date of Mailing: Aug. 24, 2006, 4 pages.
Final Office Action; U.S. Appl. No. 11/016,196; Date of Mailing: Mar. 23, 2010, 12 pages.
Final Office Action; U.S. Appl. No. 11/435,502; Date of Mailing: Mar. 29, 2010, 11 pages.
Gage, "Current Progress in Cryosurgery," Cryobiology 25, 483-486 (1988).

(56) References Cited

OTHER PUBLICATIONS

Hale et al., "Influence of chronic heat exposure and prolonged food deprivation on execretion of mahnesium, phosphorus, calcium, hydrogen ion & ketones," Aerosp Med, 1968, pp. 919-926, vol. 39—issue (9).
Heller-Page et al., "Temperature-dependent skin disorders," Journal of the American Academy of Dermatology, May 1988, vol. 18, No. 5, Pt 1, pp. 1003-1019.
Hemmingsson, "Attenuation in Human muscle and Fat Tissue in Vivo and in Vitro," Acta Radiologica Diagnosis 23, 149-151 (1982).
Henry et al.,"Les Dermatoses Hivemales," Rev Med Liege, 1999, 54:11, 864-866. [Abstract Attached].
Holman, "Variation in cryolesion penetration due to probe size and tissue thermal conductivity," Ann. Thorac. Surg. 53, 123-126 (1992).
Hong, "Patterns of Ice Formulation in Normal and Malignant Breast Tissue," Cryobiology 31, 109-120 (1994).
International Search Report and Written Opinion for PCT/US2007/023492; Applicant: Zeltiq Aesthetics, Inc.; Date of Mailing: May 15, 2008, 7 pages.
International Search Report and Written Opinion for PCT/US2007/064016; Applicant: Juniper Medical, Inc.; Date of Mailing: Jul. 20, 2007, 13 pages.
International Search Report and Written Opinion for PCT/US2007/064017; Applicant: Juniper Medical, Inc.; Date of Mailing: Oct. 26, 2007, 16 pages.
International Search Report and Written Opinion for PCT/US2007/064018; Applicant: Juniper Medical, Inc.; Date of Mailing: Jul. 26, 2007, 13 pages.
International Search Report and Written Opinion for PCT/US2007/067638; Applicant: Juniper Medical, Inc.; Date of Mailing: Jan. 10, 2008, 11 pages.
International Search Report and Written Opinion for PCT/US2007/069694; Applicant: Juniper Medical, Inc.; Date of Mailing: Nov. 23, 2007, 12 pages.
International Search Report and Written Opinion for PCT/US2007/075935; Applicant: Zeltiq Aesthetics, Inc.; Date of Mailing: Apr. 10, 2008, 12 pages.
International Search Report and Written Opinion for PCT/US2007/083255; Applicant: Zeltiq Aesthetics, Inc.; Date of Mailing: Aug. 11, 2008, 8 pages.
International Search Report and Written Opinion for PCT/US2008/073930; Applicant: Zeltiq Aesthetics, Inc.; Date of Mailing: Nov. 7, 2008, 10 pages.
International Search Report and Written Opinion for PCT/US2007/062508; Applicant: Juniper Medical, Inc.; Date of Mailing: Jul. 20, 2007, 13 pages.
International Search Report and Written Opinion for PCT/US2009/058088; Applicant: Zeltiq Aesthetics, Inc.; Date of Mailing: Nov. 20, 2009, 14 pages.
International Search Report and Written Opinion for PCT/US2009/067973; Applicant: Zeltiq Aesthetics, Inc.; Date of Mailing: Feb. 18, 2010, 10 pages.
International Search Report for EP07758558.6; Applicant: Zeltiq Aesthetics, Inc.; Mailed on Jul. 20, 2007, 4 pages.
International Search Report and Written Opinion for PCT/US2005/045988; Applicant: The General Hospital Corporation; Mailed on Apr. 25, 2006, 14 pages.
Kellum, R.E. et al., "Sclerema Neonatorum: Report of Case and Analysis of Subcutaneous and Epidermal-Dermal Lipids by Chromatographic Methods," Arch. Derm., 97:372-80, 1968.
Koska, J. et al., "Endocrine Regulation of Subcutaneous Fat Metabolism During Cold Exposure in Humans," Ann N.Y. Acad. Sci., 967:500-05, 2002.
Kundu et al., "Breath acetone analyzer: diagnostic tool to monitor dietary fat loss," Clin Chem, 1993, pp. 87-92, vol. 39, issue (1).
Kundu et al., "Novel solid-phase assay of ketone bodies in urine," Clin Chem, 1991, pp. 1565-1569, vol. 37—issue (9).

Kuroda et al., "Thermal distribution of radio-frequency inductive hyperthermia using an inductive aperture-type applicator: evaluation of the effect of tumour size and depth," Med Biol Eng Comput, 1999, pp. 285-290, vol. 37—issue (3).
Laugier, et al., "In Vivo Results with a New Device for Ultrasonic Monitoring of Pig Skin Cryosurgery: The Echographic Cryprobe," The society for Investigative Dermatology, Inc., vol. 111(2), Aug. 1998.
Levchenko, et al., "Effect of dehydration on lipid metabolism," WMJ, 1978, pp. 95-97, vol. 50—issue (1).
Lidagoster, MD et al., "Comparison of Autologous Fat Transfer in Fresh, Refridgerated, and Frozen Specimens: An Animal Model Presented," at the 16th Annual Meeting of the Northeastern Society of Plastic Surgeons: Burlington, VT, 1999, pp. 512-515.
Liu, A.Y.C. et al., "Transient Cold Shock Induces the Heat Shock Response upon Recovery at 37 C in Human Cells," J. Biol. Chem., May 20, 1994, 269(20), 14768-14775.
Lvova, "Lipid levels and lipid peroxidation in frog tissues during hypothermia and hibernation," WMJ, 1990, pp. 65-70, vol. 62—issue (1).
Maize, J.C., "Panniculitis," Cutaneous Pathology, Chapter 13:327-344, 1998.
Malcolm, G. et al., "Fatty Acid Composition of Adipose Tissue in Humans: Differences between Subcutaneous Sites." Am J Clin. Nut., 50(2):288-91, 1989.
Moschella, S.L. et al., "Diseases of the Subcutaneous Tissue," Derm., Section 2:1169-1181, 1985.
Murphy, J.V. et al., "Frostbite: Pathogensis and Treatment," The Journal of Trauma: Injury, Infection, and Critical Care, 48(1):171-178, 2000.
Nagao et al., "Dietary diacylglycerol suppresses accumulation of body fat compared to triacylglycerol in men a double-blind controlled trial," J Nutr, 2000, pp. 792-797, vol. 130—issue (4).
Nagore et al., "Lipoatrophia semicircularis—a traumatic panniculitis: Report of seven cases and review of the literature," Journal of the American Academy of Dermatology, Nov. 1998, 39:879-81.
Nielsen, "Thermoregulation in Rest and Exercise," Acta Phys Scan Supp, 1969, pp. 6-74, vol. 323.
Nishikawa, "Ultrastructural Changes and Lipid Peroxidation in Rat Adipomusculocutaneous Flap Isotransplants after Normothermic Storage and Reperfusion," Transplantation, 1992, 54, 795-801.
Non-Final Office Action; U.S. Appl. No. 10/391,221; Date of Mailing: Jul. 22, 2005, 6 pages.
Non-Final Office Action; U.S. Appl. No. 10/391,221; Date of Mailing: Jan. 25, 2006, 6 pages.
Non-Final Office Action; U.S. Appl. No. 10/391,221; Date of Mailing: May 30, 2007, 8 pages.
Non-Final Office Action; U.S. Appl. No. 11/016,196; Date of Mailing: Sep. 25, 2009, 8 pages.
Non-Final Office Action; U.S. Appl. No. 11/016,196; Date of Mailing: Apr. 22, 2008, 11 pages.
Non-Final Office Action; U.S. Appl. No. 11/359,092; Date of Mailing: Nov. 19, 2009, 13 pages.
Non-Final Office Action; U.S. Appl. No. 11/435,502; Date of Mailing: Jul. 17, 2009, 10 pages.
Non-Final Office Action; U.S. Appl. No. 11/528,225; Date of Mailing: Apr. 12, 2010, 11 pages.
Non-Final Office Action; U.S. Appl. No. 11/558,046; Date of Mailing: Jul. 12, 2010, 14 pages.
Non-Final Office Action; U.S. Appl. No. 11/741,271; Date of Mailing: Jul. 12, 2010, 9 pages.
Pease, "An Integrated Probe for Magnetic Resonance Imaging Monitored Skin Cryosurgery," Journal of Biomedical Engineering 117, 59-63, (1995).
Pech, "Attenuation values, volume changes and artifacts in tissue due to freezing," Acta Radiologica 6, 779-782 (1987).
Peterson et al., "Bilateral Fat Necrosis of the Scrotum, Urology Service, Department of Surgery, Dermatology Service, Department of Medicine and Department of Pediatrics," Letterman Army Medical Center, Journal of Urology, 1976, pp. 825-826, vol. 116, The Williams & Wilkins Co.

(56) References Cited

OTHER PUBLICATIONS

Phinney, S.D. et al., "Human Subcutaneous Adipose Tissue Shows Site-Specific Differences in Fatty Acid Composition," Am J. Clin. Nutr., 60:725-29, 1994.
Pre-Interview Office Action; U.S. Appl. No. 11/434,478; Date of Mailing: May 6, 2010, 4 pages.
Rabi, "Metabolic adaptations in brown adipose tissue of the hamster in extreme ambient temperatures." American Journal of Physiology 231, 153-160 (1976).
Renold, A.E., "Adipose Tissue," Handbook of Physiology, Chapter 15:170-76, 1965.
Rubinsky, "Cryosurgery: advances in the application of low temperatures to medicine," Int. J. Refrig. 190-199 (1991).
Schoning, et al., "Experimental Frostbite: Freezing Times, Rewarming Times, and Lowest Temperatures of Pig Skin Exposed to Chilled Air," Cryobiology, 1990, pp. 189-193, 27.
Shephard, "Adaptation to Exercise in the Cold." Sports Medicine, 1985, 2:59-71.
Winkler at al., "Gene Transfer in Laboratory Fish: Model Organisms for the Analysis of Gene Function," Transgenic Animals, 1997, pp. 387-395.
Young, H.E. et al.. "Isolation of Embryonic Chick Myosatellite and Pluripotent Stem Cells, " J. Tiss. Cult. Meth., 14:85-92, 1992.
European Search Report, European Application No. EP07758558.6; Applicant: Zeltiq Aesthetics, Inc.; Mailed on Jul. 20, 2007, 4 pages.
European Search Report, European Patent Application No. EP07761461; Applicant: Zeltiq Aesthetics, Inc., Mailing Date: Apr. 25, 2012, 9 pages.
European Search Report, Supplement, European Patent Application No. EP08798416.7, Applicant: Zeltiq Aesthetics, Inc., Mailing Date: Jan. 12, 2012, 7 pages.
European Search Report, Supplement, European Patent Application No. EP09836823, Applicant: Zeltiq Aesthetics, Inc., Mailing Date: May 15, 2012, 5 pages.
Final Office Action; U.S. Appl. No. 11/741,271; Date of Mailing: Jul. 19, 2012, 8 pages.
Final Office Action; U.S. Appl. No. 11/750,953; Date of Mailing: Jul. 5, 2012, 11 pages.
International Search Report and Written Opinion for PCT/US2012/022585; Mailed on May 18, 2012, 14 pages.
Merrill, Tom, "A Chill to the Heart: A System to Deliver Local Hypothermia Could One Day Improve the Lives of Heart-Attack Patients," Mechanical Engineering Magazine, Oct. 2010 (10 pages).
Non-Final Office Action; U.S. Appl. No. 11/528,189; Date of Mailing Apr. 6, 2012, 9 pages.
Non-Final Office Action; U.S. Appl. No. 11/777,992; Date of Mailing: Jun. 22, 2012, 5 pages.
Non-Final Office Action; U.S. Appl. No. 12/337,544; Date of Mailing: Mar. 30, 2012, 13 pgs.
Non-Final Office Action; U.S. Appl. No. 12/942,852; Date of Mailing: Mar. 7, 2011, 6 pages.

Pope, "Selective Firbous Septae Heating", Thermage Article, Feb. 2005, 7pgs.
European Search Report; Application No. EP10770461; Dated Aug. 31, 2012; Applicant: Zeltiq Aesthetics, Inc. 5 pgs.
Manstein et al. "A Novel Cryotherapy Method of Non-invasive, Selective Lipolysis" LasersSurg.Med 40:S20 p. 104 (2008).
Manstein et al."Selective Cryolysis: A Novel Method of Non-Invasive Fat Removal", LasersSurg.Med. 40:595-604 (2008).
Nagle W.A., Soloff, B.L., Moss, A.J. Jr., Henle K.J. "Cultured Chinese Hamster Cells Undergo Apoptosis After Exposure to Cold but Nonfreezing Temperatures" Cryobiology 27, 439-451 (1990).
Narins, "Non-Surgical Radiofrequency Facelift", 2003, 495-500, 6 pgs.
Mazur, P. "Cryobiology: the Freezing of Biological Systems" Science, 68: 939-949 (1970).
Rubinsky, B., "Principles of Low Temperature Preservation" Heart Failure Reviews, 8, 277-284 (2003).
Thermage, News Release, "Study Published in Facial Plastic Surgery Journal Finds Selective Heating of Fibrous Septae Key to Success and Safety of Thermage ThermoCool System", Jun. 20, 2005, 2 pages.
Vallerand, A.L., Zamecnik. J., Jones, P.J.H. Jacobs, I. "Cold Stress Increases Lipolysis, FFA RA and TG/FFA Cycling in Humans" Aviation, Space, and Environmental Medicine 70, 42-50 (1999).
Rossi, "Cellulite: a Review" 2000, 251-262, 12 pgs.
"ThermaCool Monopolar Capacitive Radiofrequency",The one choice for nonablative tissue tightening and contouring, Tech Brochure, Nov. 30, 2005, 8 pgs.
"So-Called Cellulite: An Invetnted Disease", Nurnberger, Journal Title: Journal of dermatologic surgery and oncology, Mar. 1978, 14 pgs.
"Effect of Controlled Volumetric Tissue Heating with Radiorequency on Cellulite and the Subcutaneous Tissue of the Bottocks and Thighs" Del Pino, 2006, 9 pgs.
Mayoral, "Skin Tightening with a Combined Unipolar and Bipolar Radiofrequency Device" , 2007 Journal of Drugs in Dermatology, 4 pgs.
Becker, "Local Temperature Rises Influence In Vivo Electroporation Pore Development: A Numerical Stratum Corneum Lipid Phase Transition Model", Oct. 2007, 10 pgs.
Miklavcic, "Electroporation-Based Technologies and Treatments", 2010 236:1-2, 2 pgs.
Nanda, "Studies on electroporation of thermally and chemically treated human erythrocytes", May 28, 1993 in revised form Mar. 7, 1994, 6 pgs.
BioMedical Engineering OnLine, "High-Frequency Irreversible electroporation (H-FIRE) for non-thermal ablation without muscle contraction", Nov. 21, 2011, 21 pgs.
Al-Sakere, "Tumor Ablation with Irreversible Electroporation", Nov. 2007, Issue 11, 8 pgs.

\* cited by examiner

COMBINED MODALITY TREATMENT SYSTEMS, METHODS AND APPARATUS FOR BODY CONTOURING APPLICATIONS

INCORPORATION BY REFERENCE OF COMMONLY-OWNED APPLICATIONS

The following commonly assigned U.S. Patent Applications are incorporated herein by reference in their entirety:

U.S. patent application Ser. No. 11/750,953, filed on May 18, 2007, entitled "METHOD OF ENHANCED REMOVAL OF HEAT FROM SUBCUTANEOUS LIPID-RICH CELLS AND TREATMENT APPARATUS HAVING AN ACTUATOR";

U.S. Pat. No. 6,032,675 entitled "FREEZING METHOD FOR CONTROLLED REMOVAL OF FATTY TISSUE BY LIPOSUCTION";

U.S. Patent Publication No. 2007/0255362 entitled "CRYOPROTECTANT FOR USE WITH A TREATMENT DEVICE FOR IMPROVED COOLING OF SUBCUTANEOUS LIPID-RICH CELLS";

U.S. Patent Publication No. 2007/0198071 entitled "COOLING DEVICE FOR REMOVING HEAT FROM SUBCUTANEOUS LIPID-RICH CELLS";

U.S. Patent Publication No. 2008/0077201 entitled "COOLING DEVICES WITH FLEXIBLE SENSORS";

U.S. Patent Publication No. 2008/0077211 entitled "COOLING DEVICE HAVING A PLURALITY OF CONTROLLABLE COOLING ELEMENTS TO PROVIDE A PREDETERMINED COOLING PROFILE";

U.S. patent application Ser. No. 11/933,066, filed Oct. 31, 2007, entitled "METHOD AND APPARATUS FOR COOLING SUBCUTANEOUS LIPID-RICH CELLS OR TISSUE," now abandoned;

U.S. patent application Ser. No. 11/777,995, filed Jul. 13, 2007, entitled "LIMITING USE OF DISPOSABLE PATIENT PROTECTION DEVICES," now abandoned;

U.S. patent application Ser. No. 11/777,992, filed Jul. 13, 2007, entitled "SYSTEM FOR TREATING LIPID-RICH REGIONS," now abandoned;

U.S. patent application Ser. No. 11/777,999, filed Jul. 13, 2007, entitled "MANAGING SYSTEM TEMPERATURE TO REMOVE HEAT FROM LIPID-RICH REGIONS," now abandoned;

U.S. patent application Ser. No. 11/778,003, filed Jul. 13, 2007, entitled "SECURE SYSTEM FOR REMOVING HEAT FROM LIPID-RICH REGIONS," now abandoned;

U.S. patent application Ser. No. 11/778,001, entitled "USER INTERFACES FOR A SYSTEM THAT REMOVES HEAT FROM LIPID-RICH REGIONS," filed Jul. 13, 2007, now abandoned;

U.S. Patent Publication No. 2008/0077202 entitled "TISSUE TREATMENT METHODS"; and U.S. Provisional Patent Application Ser. No. 61/100,248, filed Sep. 25, 2008, entitled "TREATMENT PLANNING SYSTEMS AND METHODS FOR BODY CONTOURING APPLICATIONS."

TECHNICAL FIELD

The present application relates generally to combined modality treatment apparatuses, systems and methods for body contouring applications including systems and methods for delivering radio frequency energy and cooling to affect subcutaneous lipid-rich cells.

BACKGROUND

Excess body fat, or adipose tissue, may be present in various locations of the body, including, for example, the thigh, buttocks, abdomen, knees, back, face, arms, and other areas. Excess adipose tissue can detract from personal appearance and athletic performance. Moreover, excess adipose tissue is thought to magnify the unattractive appearance of cellulite, which forms when subcutaneous fat lobules protrude or penetrate into the dermis and create dimples where the skin is attached to underlying structural fibrous strands. Cellulite and excessive amounts of adipose tissue are often considered to be unappealing. Moreover, significant health risks may be associated with higher amounts of excess body fat.

A variety of methods have been used to treat individuals having excess body fat and, in many instances, non-invasive removal of excess subcutaneous adipose tissue can eliminate unnecessary recovery time and discomfort associated with invasive procedures such as liposuction. Conventional non-invasive treatments for removing excess body fat typically include topical agents, weight-loss drugs, regular exercise, dieting, or a combination of these treatments. One drawback of these treatments is that they may not be effective or even possible under certain circumstances. For example, when a person is physically injured or ill, regular exercise may not be an option. Similarly, weight-loss drugs or topical agents are not an option when they cause an allergic or negative reaction. Furthermore, fat loss in selective areas of a person's body often cannot be achieved using general or systemic weight-loss methods.

Other methods designed to reduce subcutaneous adipose tissue include laser-assisted liposuction and mesotherapy. Newer non-invasive methods include applying radiant energy to subcutaneous lipid-rich cells via, e.g., radio frequency and/or light energy, such as described in U.S. Patent Publication No. 2006/0036300 and U.S. Pat. No. 5,143,063, or via, e.g., high intensity focused ultrasound (HIFU) radiation such as described in U.S. Pat. Nos. 7,258,674 and 7,347,855. Additional methods and devices for non-invasively reducing subcutaneous adipose tissue by cooling are disclosed in U.S. Pat. No. 7,367,341 entitled "METHODS AND DEVICES FOR SELECTIVE DISRUPTION OF FATTY TISSUE BY CONTROLLED COOLING" to Anderson et al. and U.S. Patent Publication No. 2005/0251120 entitled "METHODS AND DEVICES FOR DETECTION AND CONTROL OF SELECTIVE DISRUPTION OF FATTY TISSUE BY CONTROLLED COOLING" to Anderson et al., the entire disclosures of which are incorporated herein by reference.

BRIEF DESCRIPTION OF THE DRAWINGS

In the drawings, identical reference numbers identify similar elements or acts. The sizes and relative positions of elements in the drawings are not necessarily drawn to scale. For example, the shapes of various elements and angles are not drawn to scale, and some of these elements are arbitrarily enlarged and positioned to improve drawing legibility. Further, the particular shapes of the elements as drawn are not intended to convey any information regarding the actual shape of the particular elements, and have been solely selected for ease of recognition in the drawings.

DETAILED DESCRIPTION

A. Overview

Figure 1:
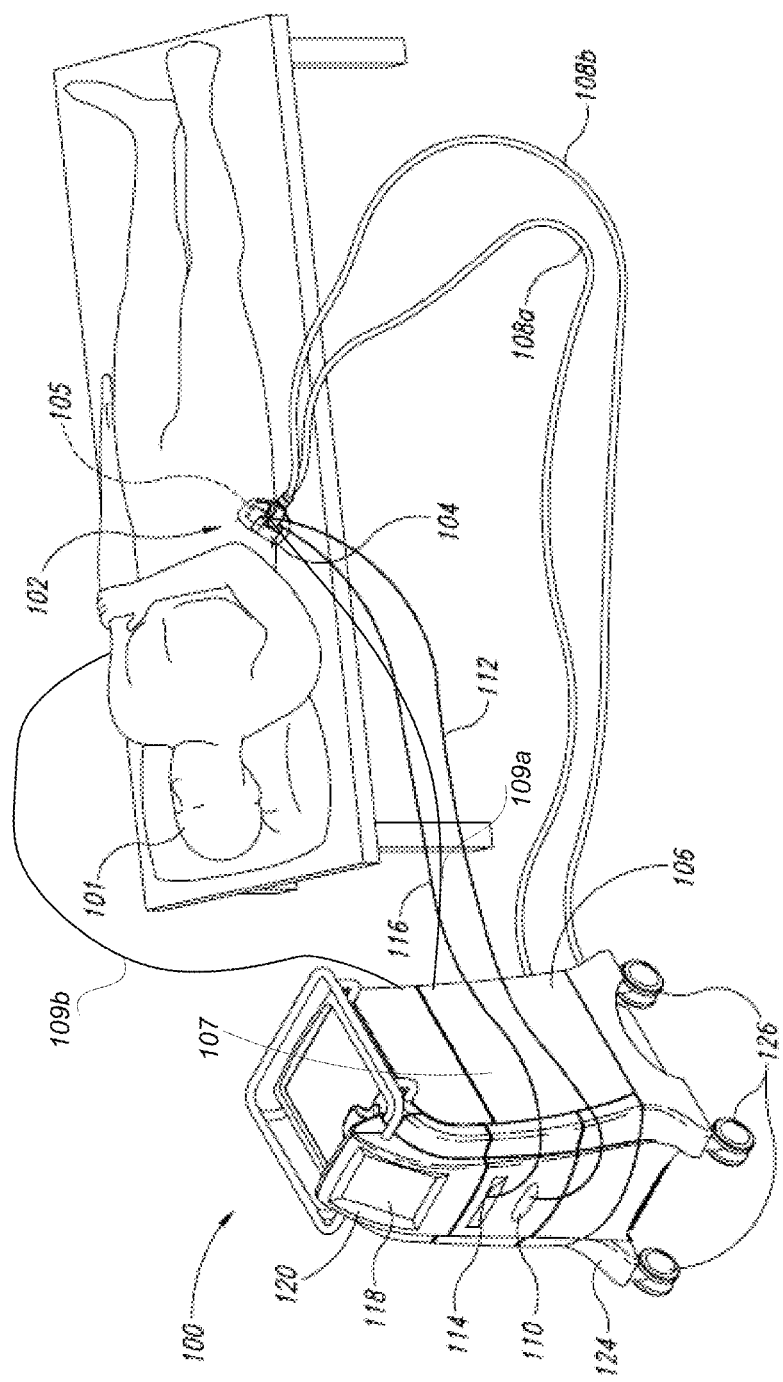
FIG. 1 is an isometric view schematically illustrating a combined modality treatment system for treating subcutaneous lipid-rich regions of a patient in accordance with an embodiment of the disclosure.

Systems, devices and methods are provided herein that enable simultaneous or sequential delivery of capacitively coupled radiofrequency (RF) energy and cooling to selectively affect targeted subcutaneous lipid-rich cells. Several of the details set forth below are provided to describe the following examples and methods in a manner sufficient to enable a person skilled in the relevant art to practice, make and use them. Several of the details and advantages described below, however, may not be necessary to practice certain examples and methods of the technology. Additionally, the technology may include other examples and methods that are within the scope of the claims but are not described in detail.

Reference throughout this specification to "one example," "an example," "one embodiment," or "an embodiment" means that a particular feature, structure, or characteristic described in connection with the example is included in at least one example of the present technology. Thus, the occurrences of the phrases "in one example," "in an example," "one embodiment," or "an embodiment" in various places throughout this specification are not necessarily all referring to the same example. Furthermore, the particular features, structures, routines, stages, or characteristics may be combined in any suitable manner in one or more examples of the technology. The headings provided herein are for convenience only and are not intended to limit or interpret the scope or meaning of the claimed technology.

Some embodiments of the disclosure are directed to methods for reducing irregularities in a surface of a subject's skin resulting from an uneven distribution of adipose tissue in the subcutaneous layer. For example, a method can include selectively heating tissue by one or more methods, such as, e.g., by delivering capacitively or conductively coupled radiofrequency (RF) energy to a target region of the subject at a frequency, duration and power. The delivered RF energy selectively heats fibrous septae in a subcutaneous layer of the target region. Furthermore, the method can include removing heat such that lipid-rich lobules in the subcutaneous layer at the target region are reduced in number and/or size to an extent while non-lipid-rich cells and lipid-rich regions adjacent to the fibrous septae are not reduced in number or size to the extent, thereby reducing irregularities in the surface of skin of the subject.

Other embodiments of the disclosure are directed to a system for non-invasive, transdermal removal of heat from subcutaneous lipid-rich cells of a subject. The system can include a treatment unit in thermal communication with a fluid chamber, wherein the fluid chamber can house and provide a coolant. The system can also include a radiofrequency (RF) energy generating unit for generating RF current, and a treatment device in fluid communication with the treatment unit and in electrical communication with the RF energy generating unit. The system can further include a controller in communication with the treatment unit, the RF energy generating unit and the treatment device. In one embodiment, the controller has instructions for causing the treatment device to capacitively or conductively couple RF energy to the subject to selectively heat connective tissue in a target region beneath an epidermis of the subject to a maximum temperature less than a collagen denaturation temperature. The treatment device can be further configured to reduce a temperature of the target region beneath the epidermis of the subject to selectively reduce the temperature of subcutaneous lipid-rich cells in the target region such that the subcutaneous lipid-rich cells are substantially affected while non-lipid rich cells in the epidermis and subcutaneous lipid-rich cells adjacent to the connective tissue are not substantially affected (e.g., damaged, injured, disrupted or destroyed).

Other aspects of the disclosure are directed toward a combined modality treatment system for selectively removing heat from subcutaneous lipid-rich cells in a target region of a subject having skin. The combined modality treatment system can include treatment unit in thermal communication with a fluid chamber, wherein the fluid chamber can house and provide a coolant. The combined modality treatment system can also include a RF energy source for generating RF current. Further, the system can include a controller and a treatment device. The treatment device can include a heat exchange plate coupled to the RF energy source and a thermoelectric cooling element in communication with the treatment unit. In one embodiment, the controller includes instructions that cause the treatment device to capacitively or conductively couple radiofrequency (RF) energy to the skin of the subject to selectively heat fibrous septae in the target region to a final temperature less than a fibrous septae denaturation temperature. The controller can also include instructions that cause the treatment device to remove heat from the subcutaneous lipid-rich cells of the subject during a treatment process such that subcutaneous lipid-rich cells are substantially affected while non-lipid-rich cells and subcutaneous lipid-rich cells adjacent to the fibrous septae are not substantially affected.

B. Combined Modality Treatment System

FIG. 1 and the following discussion provide a brief, general description of an example of a combined modality treatment system 100 in which aspects of the disclosure can be implemented. Those skilled in the relevant art will appreciate that other examples of the disclosure can be practiced with other treatment systems and treatment protocols, including invasive, minimally invasive, other non-invasive medical treatment systems, and/or combinations of one or more of the above for treating a patient. In general, the term "treatment system", as used generally herein, refers to any of the above system categories of medical treatment as well as any treatment regimes or medical device usage.

In one embodiment, the combined modality treatment system 100 is suitable for treating a subject's subcutaneous adipose tissue, including such as by cooling. The term "subcutaneous tissue" means tissue lying beneath the dermis and includes subcutaneous fat, or adipose tissue, which primarily is composed of lipid-rich cells, or adipocytes. When cooling the subcutaneous tissues to a temperature lower than 37° C., subcutaneous lipid-rich cells can selectively be affected. In general, the epidermis and dermis of the patient 101 have lower amounts of lipids compared to the underlying lipid-rich cells forming the subcutaneous tissues. Because non-lipidrich cells usually can withstand colder temperatures better than lipid-rich cells, the subcutaneous lipid-rich cells can selectively be affected while maintaining the integrity of the non-lipid-rich cells in the dermis and epidermis. In some embodiments, the treatment system 100 can apply cooling temperatures to the skin of the patient in a range of from about −20° C. to about 20° C. In other embodiments, the cooling temperatures can be from about −20° C. to about 10° C., from about −15° C. to about 5° C., or from about −10° C. to about 0° C.

Without being bound by theory, the selective effect of cooling on lipid-rich cells is believed to result in, for example, membrane disruption, shrinkage, disabling, destroying, removing, killing, or another method of lipid-rich cell alteration. Such alteration is believed to be an intermediate and/or final result of one or more mechanisms acting alone or in combination. It is thought that such mechanism or mechanisms trigger an apoptotic cascade, which is believed to be the dominant form of lipid-rich cell death by non-invasive cooling.

Apoptosis, also referred to as "programmed cell death", is a genetically-induced death mechanism by which cells self-destruct without incurring damage to surrounding tissues. An ordered series of biochemical events induce cells to morphologically change. These changes include cellular blebbing, loss of cell membrane asymmetry and attachment, cell shrinkage, chromatin condensation, and chromosomal DNA fragmentation. Injury via an external stimulus, such as cold exposure, is one mechanism that can induce apoptosis in cells. Nagle, W. A., Soloff, B. L., Moss, A. J. Jr., Henle, K. J. "Cultured Chinese Hamster Cells Undergo Apoptosis After Exposure to Cold but Nonfreezing Temperatures" *Cryobiology* 27, 439-451 (1990).

One aspect of apoptosis, in contrast to cellular necrosis (a traumatic form of cell death causing local inflammation), is that apoptotic cells express and display phagocytic markers on the surface of the cell membrane, thus marking the cells for phagocytosis by, for example, macrophages. As a result, phagocytes can engulf and remove the dying cells (e.g., the lipid-rich cells) without eliciting an immune response. Temperature exposures that elicit these apoptotic events in lipid-rich cells may contribute to long-lasting and/or permanent reduction and reshaping of subcutaneous adipose tissue.

Without being bound by theory, one mechanism of apoptotic lipid-rich cell death by cooling is believed to involve localized crystallization of lipids within the adipocytes at temperatures that do not induce crystallization in non-lipid-rich cells. The crystallized lipids may selectively injure these cells, inducing apoptosis (and may also induce necrotic death if the crystallized lipids damage or rupture the bilayer lipid membrane of the adipocyte). Another mechanism of injury involves the lipid phase transition of those lipids within the cell's bilayer lipid membrane, which results in membrane disruption, thereby inducing apoptosis. This mechanism is well documented for many cell types and may be active when adipocytes, or lipid-rich cells, are cooled. Mazur, P., "Cryobiology: the Freezing of Biological Systems" Science, 68: 939-949 (1970); Quinn, P. J., "A Lipid Phase Separation Model of Low Temperature Damage to Biological Membranes" Cryobiology, 22: 128-147 (1985); Rubinsky, B., "Principles of Low Temperature Preservation" *Heart Failure Reviews*, 8, 277-284 (2003). Other yet-to-be understood apoptotic mechanisms may exist, based on the relative sensitivity of lipid-rich cells to cooling compared to non-lipid rich cells.

In addition to the apoptotic mechanisms involved in lipid-rich cell death, local cold exposure may induce lipolysis (i.e., fat metabolism) of lipid-rich cells. For example, cold stress has been shown to enhance rates of lipolysis from that observed under normal conditions which serves to further increase the volumetric reduction of subcutaneous lipid-rich cells. Vallerand, A. L., Zamecnik. J., Jones, P. J. H., Jacobs, I. "Cold Stress Increases Lipolysis, FFA Ra and TG/FFA Cycling in Humans" *Aviation, Space and Environmental Medicine* 70, 42-50 (1999).

Cellulite (Gynoid lipodystrophy) typically is a hormonally mediated condition characterized by the uneven distribution of adipose tissue in the subcutaneous layer that gives rise to an irregular, dimpled skin surface common in women. Cellulite-prone tissue can be characterized by the uneven thickness and distribution of some fibrous septae strands. Piérard, G. E., Nizet, J. L, Piérard-Franchimont, C., "Cellulite: From Standing Fat Herniation to Hypodermal Stretch Marks," *Am. J. Dermatol.* 22:1, 34-37 (2000). Cellulite has proved to be a difficult and vexing problem to treat, although the demand for an effective treatment has been and remains quite high.

Figure 2:
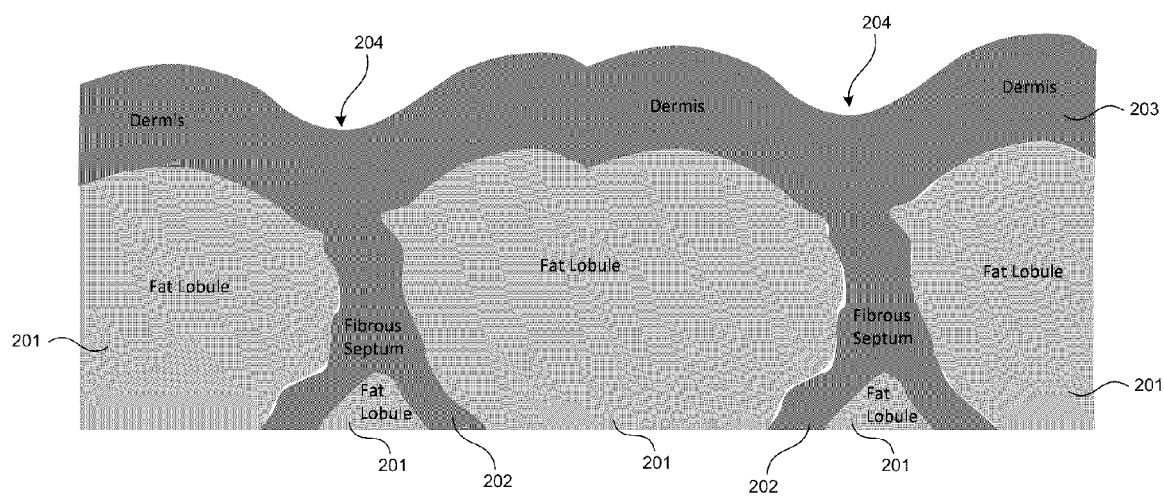
FIG. 2 is a schematic cross-sectional view of the skin and subcutaneous tissue of a subject.

As shown schematically in FIG. 2, adipose tissue is subdivided into fat cell chambers or lobules (also called "papillae adiposae") 201 by connective collagenous tissue called fibrous septae 202. The fibrous septae 202, which for females tend to generally be oriented perpendicular to the skin surface and anchor the dermal layers 203 to the underlying fascia and muscle (not shown), are organized within the subcutaneous layer to form a connective web around the adipose cells or fat lobules 202. Subcutaneous adipose cells and their lobules. 202 are not uniformly distributed throughout the subcutaneous tissue layer (e.g., between the dermis and the muscle layers), but exhibit regional differences in size and shape. These regional differences can, in part, be due to gender, age, genetics, hormones and physical conditioning among other physiological factors. The number, size, distribution and orientation of fibrous septae 202 also vary by body location, gender and age. For example, as described above, histological studies have shown that fibrous septae architecture in females differs from that in males.

In males, fibrous septae 202 tend to form an intersecting network that divide the papillae adiposae into small, polygonal units. In contrast, fibrous septae 202 in some females may tend to be oriented perpendicularly to the cutaneous surface, creating fat cell chambers that are columnar in shape and sequestered by the connective strands and the overlaying dermis layer 203 (see, e.g., FIG. 2). When the intersecting fibrous septae 202 are more uniform in size and elasticity as is characteristic of males, the forces within and between the fibrous septae and their surrounding tissue tend to be distributed relatively evenly. However, the columnar architecture of the fibrous septae 202 found in some females can result in an uneven distribution of forces throughout the subcutaneous tissue. In particular, and without being bound by theory, it is believed that this uneven distribution of forces is partially manifested by the columnar fibrous septae 202 being held in a state of tension by the underlying fascia and other tissue, resulting in a tethering or anchoring effect at the point where each such septum 202 connects with the dermal tissue 203. This tethering or anchoring is in turn manifested at the skin surface as a low spot 204 relative to adjacent dermal tissue 203 not directly above such septae, which tends to herniate as the papillae adiposae bulge into the dermal tissue 203. When viewed over a larger scale of a few square centimeters, the non-homogeneous nature of the skin surface's relative high and low points results in a dimpled or irregular appearance characteristic of cellulite.

As described above, cooling the subcutaneous tissues to a temperature lower than 37° C. selectively can affect lipid-rich cells. Cooling the lipid-rich cells of the subcutaneous layer tends uniformly to affect the adipose cells distributed throughout the subcutaneous tissue at a given depth below the dermis, for instance, when such lipid-rich cells are cooled non-invasively. As with the epidermal and dermal layers of the patient 101, however, the fibrous septae 202 generally are not affected by such treatment temperatures. To selectively treat the bulging or herniating adipose cells near the dermal—subcutaneous interface associated with cellulite conditions, the combined modality treatment system 100 can further be configured to selectively remove heat from (i.e., cool) the bulging and/or herniating fat lobules near the dermal layer and distal from the tethering fibrous septae 202, while limiting the disruption of adipose tissue near the septae, which lie near the low spots. Such selective disruption of the fat lobules 201 that constitute the high spots will have the general effect of flattening the overall contour of the skin.

Accordingly, in one embodiment, the combined modality treatment system 100 is configured to not only cool subcutaneous tissue as described herein but also to selectively heat tissue such as the fibrous septae 202 and certain adipose tissue according to the methods described herein. One method of selectively heating such tissue is by the delivery of radiofrequency (RF) energy, including for example capacitively coupled RF energy, such as a low-level monopolar RF energy as well as conductively coupled RF energy, to the subcutaneous tissue selectively to heat regions of tissue bound by the connective web of fibrous septae. Adipose cells are composed almost entirely of lipids, which generally have low thermal and electrical conductivities relative to other tissue. In contrast, fibrous septae have similar properties to the dermis and, for example, have been shown to conduct electrical energy more efficiently. Due to this high electrical and thermal conductivity of fibrous septae relative to lipids in adipose cells, the connective strands can provide a path of least resistance for capacitively or inductively coupled RF current traveling via, e.g., the surface of the skin through the epidermis and dermis, and around subcutaneous adipose tissue RF current, (which is high frequency current in the frequency range of about 0.3 MHz to about 100 MHz or higher, or in some embodiments in the range of about 0.3 MHz to about 40 MHz, while in other embodiments in the range of about 0.3 MHz to about 6 MHz), produces a thermal effect on living tissue depending on the electrical properties of the tissue. Other methods of applying energy to selectively heat tissue as described herein may be used in addition to or in place of RF energy, including, e.g., optical (e.g., laser light), acoustic (e.g., ultrasound), infrared, microwave, etc.

Figure 3:
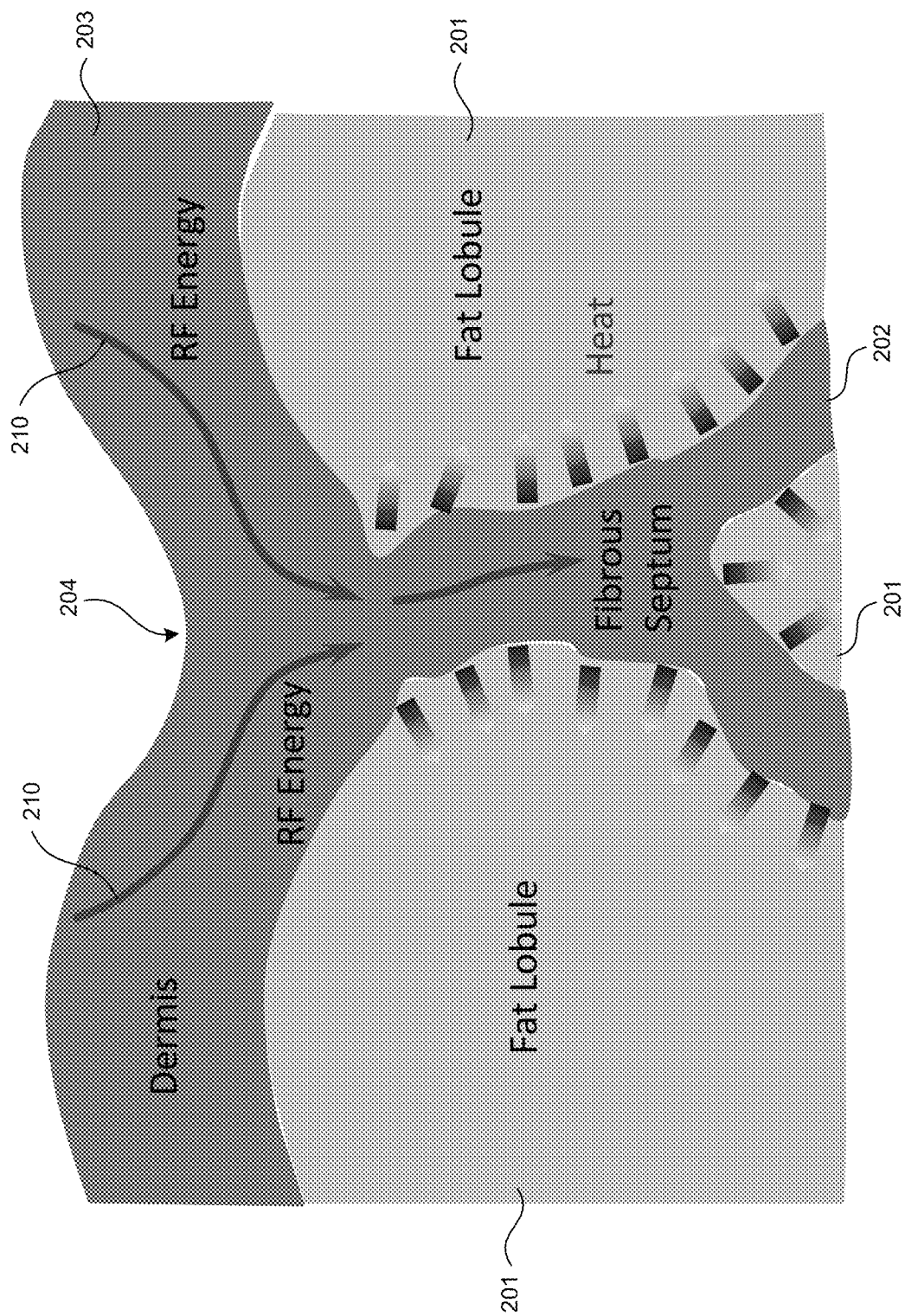
FIG. 3 is a schematic cross-sectional view of the skin and subcutaneous tissue of a subject illustrating the application of RF current thereto.

A schematic depiction of the application of energy such as RF current 210 to a region of dimpled tissue near a fibrous septum 202 is shown in FIG. 3. As RF current 210 is applied via an electrode as described herein, the current 210 concentrates in the dermal and connective tissue such as the fibrous septum 202 as described above. Heating generated by application of this RF current, depicted by arrows 210, heats the fibrous septum 202 and selected of the adipose cells in the fat lobules 201 adjacent the fibrous septum 202. In the combined modality therapy associated with the embodiments described herein, the treatment parameters may be adjusted selectively to affect, in connection with cooling the subcutaneous tissue, the temperature profile of and the number of the adipose cells in the lobules 201 that are heated via the application of such RF current. For example, RF power in the range of about 0.02 to about 10 W/cm$^2$ or higher during cooling can have the desired effect of warming the affected fibrous septae 202 and the fat lobules in a region near the affected fibrous septae 202 while allowing the cooling and subsequent selective reduction of fat lobules 201 more distal from the fibrous septae 202.

Heat is generated by the tissue's natural resistance to the flow of current (e.g., movement of electrons and ions) within an electrical field as a reaction to the rapid change of polarity. This electrical field changes polarity at a desired rate (e.g., at approximately 0.3 to approximately 100 MHz), and the charged particles within the electric field change orientation at that same frequency. The tissue's natural resistance to the movement of these charged ions and molecules in the skin and subcutaneous tissue generates heat. Pope, K., Levinson, M., Ross, E. V., "Selective Fibrous Septae Heating: An Additional Mechanism of Action for Capacitively Coupled Monopolar Radiofrequency," *Thermage, Inc.* (2005).

In accordance with one embodiment, RF energy is generated and applied to a target region of the patient 101 while simultaneously cooling the subcutaneous tissues to a temperature lower than 37° C. in a manner that (a) selectively heats the fibrous septae and the adipose tissue adjacent to the fibrous septae, and (b) selectively affects the lipid-rich cells in regions of thinning or absent fibrous septae. In some embodiments, the fibrous septae are heated to a maximum temperature less than a fibrous septae denaturation temperature. Thermal energy is known to denature collagenous tissue, such as fibrous septae, at temperatures of approximately 65° C. (e.g., between 60° C. and 80° C.). Therefore, in one embodiment, the capacitively coupled RF energy is delivered to the target region of the patient such that the fibrous septae are heated to a temperature approximately less than 60° C.

In some embodiments, the treatment system 100 can apply RF current to the skin of the patient while/during cooling treatment in a simultaneous manner, or in a sequential manner, such that the fibrous septae are warmed to a range of from about 0° C. to about 60° C. In other embodiments, the fibrous septae can be warmed to temperatures from about 10° C. to about 30° C., from 5° C. to about 20° C., or from about 0° C. to about 10° C. For example, capacitively coupled RF energy can be delivered to the target region of the patient 101 such that the lipid-rich cells adjacent to the fibrous septae are not cooled to temperatures below approximately 10° C.-15° C., while allowing the lipid-rich cells remote from the fibrous septae or near thinning fibrous septae strands to cool to a temperature below approximately 10° C.

In some embodiments, RF energy can be applied to the target region of the patient 101 simultaneously with cooling (i.e., removing heat) such that a controllable temperature difference is maintained between (a) the fibrous septae and tissue adjacent to the fibrous septae, and (b) bulging or herniating adipose tissue spaced apart or otherwise separated from the fibrous septae. In other embodiments, the RF energy can be applied to the target region before, periodically during, or after cooling for selectively affecting bulging or herniating adipose tissue in the subcutaneous layer of the patient 101.

In various embodiments, the combined modality treatment system 100 includes a controller, a computing device, a data acquisition device, a treatment unit, an RF energy generating unit and one or more applicators. The system 100 can employ these components in various embodiments to receive a selection of a treatment profile and apply the selected treatment using an applicator.

FIG. 1 is an isometric view schematically illustrating a combined modality treatment system 100 for selectively heating fibrous septae and removing heat from herniated and/or bulging subcutaneous lipid-rich regions of a subject patient 101 in accordance with an embodiment of the disclosure. The system 100 can include a combined modality device 104 including an applicator 105 that engages a target region of the subject 101, such as the abdominal region 102. It will be understood that combined modality devices 104 and applicators 105 can be provided having various shapes and sizes suitable for different body regions and body parts such that any suitable area for removing heat from a subcutaneous lipid-rich region of the subject 101 can be achieved.

An applicator, such as applicator 105, is a component of the system 100 that both cools subcutaneous tissue and selectively heats subcutaneous fibrous septae in a region of a subject 101, such as a human or animal (i.e., "patient"). Various types of applicators may be applied during treatment, such as a vacuum applicator, a belt applicator (either of which may be used in combination with a massage or vibrating capability), and so forth. Each applicator may be designed to treat identified portions of the patient's body, such as chin, cheeks, arms, pectoral areas, thighs, calves, buttocks, abdomen, "love handles", back, and so forth. For example, the vacuum applicator may be applied at the back region, and the belt applicator can be applied around the thigh region, either with or without massage or vibration. Exemplary applicators and their configurations usable or adaptable for use with the combined modality treatment system 100 variously are described in, e.g., commonly assigned U.S. Patent Publication Nos. 2007/0198071, 2008/0077201, and 2008/0077211 and in U.S. patent application Ser. No. 11/750,953. In further embodiments, the system 100 may also include a patient protection device (not shown) incorporated into or configured for use with the applicator that prevents the applicator from directly contacting a patient's skin and thereby reducing the likelihood of cross-contamination between patients, minimizing cleaning requirements for the applicator. The patient protection device may also include or incorporate various storage, computing, and communications devices, such as a radio frequency identification (RFID) component, allowing for example, use to be monitored and/or metered. Exemplary patient protection devices are described in commonly assigned U.S. Patent Publication No. 2008/0077201.

In the present example, the system 100 can also include a treatment unit 106 and supply and return fluid lines 108a-b between the combined modality treatment device 104 and the treatment unit 106. A treatment unit 106 is a device that, based on variable power input, can increase or decrease the temperature at a connected combined modality treatment device 104 that in turn may be attached to or incorporated into the applicator 105. The treatment unit 106 can remove heat from a circulating coolant to a heat sink and provide a chilled coolant to the combined modality treatment device 104 via the fluid lines 108a-b. Alternatively, treatment unit 106 can circulate warm coolant to the combined modality treatment device 104 during periods of warming. Examples of the circulating coolant include water, glycol, synthetic heat transfer fluid, oil, a refrigerant, and/or any other suitable heat conducting fluid. The fluid lines 108a-b can be hoses or other conduits constructed from polyethylene, polyvinyl chloride, polyurethane, and/or other materials that can accommodate the particular circulating coolant. The treatment unit 106 can be a refrigeration unit, a cooling tower, a thermoelectric chiller, or any other device capable of removing heat from a coolant. Alternatively, a municipal water supply (e.g., tap water) can be used in place of the treatment unit 106. One skilled in the art will recognize that there are a number of other cooling technologies that could be used such that the treatment unit or chiller need not be limited to those described herein.

The system 100 can further include an RF energy generating unit 107 and RF power lines 109a-b between the treatment device 104, an RF current return electrode (not shown) and the RF energy generating unit 107. The RF energy generating unit 107 can include a variable powered RF generator capable of generating and delivering RF energy through the RF power line 109a to one or more RF electrodes, or other electrically conductive material that can be charged with RF current, in the combined modality treatment device 104 for capacitively coupling radiofrequency (RF) energy to the target region of the subject 101. One advantage among several of a system using capacitively coupled RF energy in the various embodiments described herein is the ability to reduce or eliminate electrode edge effects. In particular, and as described below, a dielectric layer or film may be used on the one or more RF electrodes to increase the impedance of the electrode and produce a more uniform current flow through the electrode to the skin of the patient. Such a layer or film creates a capacitance effect whose magnitude and other qualities may be controlled by the composition, surface area and thickness of the layer, the choice of methods by which the layer or film is deposited and/or adhered to the RF electrode, and the frequency of the RF signal.

Alternatively, system 100 can be configured to conductively couple RF energy to a patient. This may be accomplished by, e.g., the use of an RF electrode without a dielectric layer or film. The choice of whether to use a capacitively coupled RF system or a conductively-coupled RF system may be predicated upon the particular design of the electrode, the location on the patient which the system 100 is used, frequency and power settings, temperatures, treatment duration, and other such parameters and other considerations.

In this example, the combined modality treatment device 104 includes at least one applicator 105 and is associated with at least one treatment unit 106. The applicator 105 can provide mechanical energy to create a vibratory, massage, and/or pulsatile effect. The applicator 105 can include one or more actuators, such as, motors with eccentric weight, or other vibratory motors such as hydraulic motors, electric motors, pneumatic motors, solenoids, other mechanical motors, piezoelectric shakers, and so on, to provide vibratory energy or other mechanical energy to the treatment site. Further examples include a plurality of actuators for use in connection with a single combined modality treatment device 104 and/or applicator 105 in any desired combination. For example, an eccentric weight actuator can be associated with one combined modality treatment device 104 or applicator 105, while a pneumatic motor can be associated with another section of the same treatment device or applicator. This, for example, would give the operator of the treatment system 100 options for differential treatment of lipid rich cells within a single region or among multiple regions of the subject 101. The use of one or more actuators and actuator types in various combinations and configurations with a combined modality treatment device 104 or applicator 105 may be possible.

The combined modality treatment device 104 can include one or more heat exchanging units. The heat exchanging unit can be a Peltier-type thermoelectric element, and the combined modality treatment device 104 can have multiple individually controlled heat exchanging units (e.g., between 1 and 50, between 10 and 45; between 15 and 21, approximately 100, etc.) to create a custom spatial cooling profile and/or a time-varying cooling profile. Each custom treatment profile can include one or more segments, and each segment can include a specified duration, a target temperature, and control parameters for features such as vibration, massage, vacuum, and other treatment modes. Treatment devices having multiple individually controlled heat exchanging units are described in commonly assigned U.S. Patent Publication No. 2008/0077211, U.S. Provisional Application No. 61/298,175, filed Jan. 25, 2010, and U.S. Provisional Application No. 61/354,615 filed Jun. 14, 2010.

Additionally, the combined modality treatment device 104 can include one or more RF electrodes. For example, the RF electrodes can be a single electrode or a plurality of electrodes positioned in a desired or segmented arrangement and can form a segmented flexible circuit. In another embodiment, the treatment device 104 can include an electrically conductive material, such as aluminum, that can be charged with RF current. RF power can be delivered to the RF electrodes via RF power line 109a and, thereafter, coupled to the target region of the subject 101 to achieve selective heating of the underlying fibrous septae collagen network and adjacent adipose tissue. Generally, RF electrodes can be monopolar or bipolar. Capacitively coupled monopolar RF current flows from the electrode into the epidermis and dermis, through the subcutaneous tissue via conduction along the less-resistant fibrous septae and into the muscle tissue (at which location it ideally has dissipated to a level that it does not have any appreciable effect thereon). The RF current continues to flow through the body to a return electrode (not shown) adhered to a second site on the patient and then returns to the RF energy generating unit 107 via line 109b.

Alternatively, the treatment device 104 may operate without a return electrode and line 109b. The return RF current flows out of the body and through the air to the RF energy generating unit 107 to complete the circuit. The frequency in such a configuration, sometimes referred to a "unipolar" configuration, can be between about 30 MHz and about 50 MHz. In another embodiment, the frequency for such a configuration is between about 35 MHz and about 45 MHz. In yet another embodiment, the frequency for such a configuration is about 40 MHz.

The system 100 can further include a power supply 110 and a controller 114 operatively coupled to the combined modality treatment device 104 and the applicator 105. In one embodiment, the power supply 110 can provide a direct current voltage to the thermoelectric treatment device 104 and/or the applicator 105 to remove heat from the subject 101. The controller 114 can monitor process parameters via sensors (not shown) placed proximate to the combined modality treatment device 104 via a control line 116 to, among other things, adjust the heat removal rate and/or RF energy delivery rate based on the process parameters. The controller 114 can further monitor process parameters to adjust the applicator 105 based on treatment parameters, such as treatment parameters defined in a custom treatment profile or patient-specific treatment plan.

The controller 114 can exchange data with the applicator 105 via an electrical line 112 or, alternatively, via a wireless or an optical communication link. Note that control line 116 and electrical line 11.2 are shown in FIG. 1 without any support structure. Alternatively, control line 116 and electrical line 112 (and other lines including, but not limited to fluid lines 108a-b and RF power lines 109a-b) may be bundled into or otherwise accompanied by a conduit or the like to protect such lines, enhance ergonomic comfort, minimize unwanted motion (and thus potential inefficient removal of heat from and/or delivery of RF energy to subject 101), and to provide an aesthetic appearance to system 100. Examples of such a conduit include a flexible polymeric, fabric, or composite sheath, an adjustable arm, etc. Such a conduit (not shown) may be designed (via adjustable joints, etc.) to "set" the conduit in place for the treatment of subject 101.

The controller 114 can include any processor, Programmable Logic Controller, Distributed Control System, secure processor, and the like. A secure processor can be implemented as an integrated circuit with access-controlled physical interfaces; tamper resistant containment; means of detecting and responding to physical tampering; secure storage; and shielded execution of computer-executable instructions. Some secure processors also provide cryptographic accelerator circuitry. Secure storage may also be implemented as a secure flash memory, secure serial EEPROM, secure field programmable gate array, or secure application-specific integrated circuit.

In another aspect, the controller 114 can receive data from an input device 118 (shown as a touch screen), transmit data to an output device 120, and/or exchange data with a control panel (not shown). The input device 118 can include a keyboard, a mouse, a stylus, a touch screen, a push button, a switch, a potentiometer, a scanner, or any other device suitable for accepting user input. The output device 120 can include a display or touch screen, a printer, video monitor, a medium reader, an audio device, any combination thereof, and any other device or devices suitable for providing user feedback.

In the embodiment of FIG. 1, the output device 120 is a touch screen that functions as both an input device 118 and an output device 120. The control panel can include visual indicator devices or controls (e.g., indicator lights, numerical displays, etc.) and/or audio indicator devices or controls. The control panel may be a component separate from the input device 118 and/or output device 120, may be integrated with one or more of the devices, may be partially integrated with one or more of the devices, may be in another location, and so on. In alternative examples, the control panel, input device 118, output device 120, or parts thereof (described herein) may be contained in, attached to, or integrated with the combined modality treatment device 104 and/or applicator 105. In this example, the controller 114, power supply 110, control panel, treatment unit 106, input device 118, and output device 120 are carried by a rack 124 with wheels 126 for portability. In alternative embodiments, the controller 114 can be contained in, attached to, or integrated with the combined modality treatment device 104 and/or the applicator 105 and/or the patient protection device described above. In yet other embodiments, the various components can be fixedly installed at a treatment site. Further details with respect to components and/or operation of combined modality treatment device 104, treatment unit 106, applicator 105 and other components may be found in commonly-assigned U.S. patent application Ser. No. 11/750,953.

In operation, and upon receiving input to start a treatment protocol, the controller 114 can cause the applicator 105 to cycle through each segment of a prescribed treatment plan. In so doing, the applicator 105 applies power to one or more combined modality treatment devices 104, such as thermoelectric coolers (e.g., TEC "zones"), to begin a cooling cycle and, for example, activate features or modes such as vibration, massage, vacuum, etc. Additionally, the RF energy generating unit 107 is used to generate and transfer RF energy to the RF electrodes in the one or more combined modality treatment devices 104 to begin selectively heating the fibrous septae in the subcutaneous tissue in the target region of the subject 101.

Using temperature sensors (not shown) proximate to the one or more combined modality treatment devices 104, the patient's skin, a patient protection device, or other locations or combinations thereof, the controller 114 determines whether a temperature or heat flux is at a sufficient temperature close to the target temperature or heat flux. It will be appreciated that while a region of the body (e.g., adipose tissue) has been cooled or heated to the target temperature, in actuality that region of the body may be close but not equal to the target temperature, e.g., because of the body's natural heating and cooling variations. Thus, although the system may attempt to heat or cool the tissue to the target temperature or to provide by a target heat flux, a sensor may measure a sufficiently close temperature. If the target temperature has not been reached, power can be increased or decreased to change heat flux to maintain the target temperature or "setpoint" to selectively affect bulging or herniating adipose lobules at or near the interface between the dermis and subcutaneous tissue, or to affect adipose tissue spaced apart from anchoring fibrous septae in the subcutaneous layer.

When the prescribed segment duration expires, the controller 114 may apply the temperature and duration indicated in the next treatment profile segment. In some embodiments, temperature can be controlled using a variable other than, or in addition to, power.

In some embodiments, heat flux measurements can indicate other changes or anomalies that can occur during treatment administration. For example, an increase in temperature detected by a heat flux sensor can indicate a freezing event at the skin or underlying tissue (i.e., dermal tissue). An increase in temperature as detected by the heat flux sensors can also indicate movement associated with the applicator, causing the applicator to contact a warmer area of the skin, for example. Methods and systems for collection of feedback data and monitoring of temperature measurements are described in commonly assigned U.S. patent application Ser. No. 12/196, 246, entitled "MONITORING THE COOLING OF SUBCUTANEOUS LIPID-RICH CELLS, SUCH AS THE COOLING OF ADIPOSE TISSUE," filed on Aug. 21, 2008, which is incorporated herein in its entirety by reference.

The combined modality treatment devices 104 may also include additional sensors to detect process treatment feedback. For example, thermal sensors can be included on the combined modality treatment device 104 and/or the RF energy generating unit 107 to measure voltage and current that is delivered to the target region of the subject 101. Thermal sensor output can be used, by the controller 114 for example, to control the delivery of RF power to the RF electrodes, the temperature of the electrodes or the desired temperature of the fibrous septae tissue during a treatment session. Additional sensors may be included for measuring tissue impedance, treatment application force, tissue contact with the applicator and RF energy interaction with the skin of the subject 101 among other process parameters.

In one embodiment, feedback data associated with RF energy delivery and heat removal from lipid-rich lobules in the subcutaneous layer can be collected in real-time. Real-time collection and processing of such feedback data can be used in concert with treatment administration to ensure that the process parameters used to reduce irregularities in a surface of subject's skin and adipose tissue are administered correctly and efficaciously.

Although a noninvasive applicator is illustrated and discussed herein, minimally invasive applicators may also be employed. In such a case, the applicator and patient protection device may be integrated. As an example, a cryoprobe that may be inserted directly into the subcutaneous adipose tissue to cool or freeze the tissue is an example of such a minimally invasive applicator. Cryoprobes manufactured by, e.g., Endocare, Inc., of Irvine, Calif. are suitable for such applications. This patent application incorporates by reference U.S. Pat. No. 6,494,844, entitled "DEVICE FOR BIOPSY AND TREATMENT OF BREAST TUMORS"; U.S. Pat. No. 6,551,255, entitled "DEVICE FOR BIOPSY OF TUMORS"; U.S. Publication No. 2007-0055173, entitled "ROTATIONAL CORE BIOPSY DEVICE WITH LIQUID CRYOGEN ADHESION PROBE"; U.S. Pat. No. 6,789,545, entitled "METHOD AND SYSTEM FOR CRYOABLATING FIBROADENOMAS"; U.S. Publication No. 2004-0215294, entitled "CRYOTHERAPY PROBE"; U.S. Pat. No. 7,083,612, entitled "CRYOTHERAPY SYSTEM"; and U.S. Publication No. 2005-0261753, entitled "METHODS AND SYSTEMS FOR CRYOGENIC COOLING".

According to examples of the system 100, the applicator 105 and the combined modality treatment device 104 combine to enhance disruption of cooled adipose tissue while preserving warmed adipose tissue adjacent fibrous septae strands. Further, the examples can provide reduced treatment time, reduced discomfort to the patient, and increased efficacy of treatment.

Examples of the system may provide the combined modality treatment device 104 and the applicator 105 which damage, injure, disrupt or otherwise reduce subcutaneous lipid-rich cells contributing to cellulite generally without collateral damage to non-lipid-rich cells or lipid-rich cells adjacent to selectively heated fibrous septae in the treatment region. In general, it is believed that lipid-rich cells can selectively be affected (e.g., damaged, injured, or disrupted) by exposing such cells to low temperatures that do not so affect non-lipid-rich cells. Moreover, as discussed above, RF energy can be administered simultaneously and/or in consecutive fashion to selectively heat (e.g., warm) fibrous septae in the treatment region so as to warm adjacent adipose tissue. As a result, lipid-rich cells, such as subcutaneous adipose tissue that is bulging and/or herniating into the dermis layer, can be damaged while other cells in the same region are generally not damaged even though the non-lipid-rich cells at the surface may be subject to even lower temperatures. The mechanical energy provided by the applicator may further enhance the effect on lipid-rich cells by mechanically disrupting the affected lipid-rich cells.

In some examples of the system 100, a cryoprotectant is used with the treatment device to, among other advantages, assist in preventing freezing of non lipid-rich tissue (e.g., dermal tissue) during treatment as is described in commonly-assigned U.S. Patent Publication No. 2007/0255362.

In one mode of operation, the applicator 105 is coupled to a combined modality treatment device 104. The treatment device may be configured to be a handheld device such as the device disclosed in commonly-assigned U.S. patent application Ser. No. 11/359,092, filed on Feb. 22, 2006, entitled COOLING DEVICE FOR REMOVING HEAT FROM SUBCUTANEOUS LIPID-RICH CELLS, which is incorporated by reference in its entirety.

Applying the combined modality treatment device 104 with pressure or with a vacuum type force to the subject's skin or pressing against the skin can be advantageous to achieve efficient treatment. In general, the subject 101 has a body temperature of about 37° C., and the blood circulation is one mechanism for maintaining a constant body temperature. As a result, blood flow through the skin and subcutaneous layer of the region to be treated can be viewed as a heat source that counteracts the cooling of the subdermal fat. As such, cooling the tissue of interest requires not only removing the heat from such tissue but also that of the blood circulating through this tissue. Thus, temporarily reducing or eliminating blood flow through the treatment region, by means such as, e.g., applying the treatment device with pressure, can improve the efficiency of tissue cooling and avoid excessive heat loss through the dermis and epidermis. Additionally, a vacuum can pull skin away from the body which can assist in cooling targeted underlying tissue.

By cooling the subcutaneous tissue to a temperature lower than 37° C., subcutaneous lipid-rich cells selectively can be damaged. In general, the epidermis and dermis of the subject 101 have lower amounts of lipids compared to the underlying lipid-rich cells forming the subcutaneous tissues. Because non-lipid-rich cells usually can withstand colder temperatures better than lipid-rich cells, the subcutaneous lipid-rich cells can be selectively injured while maintaining the non-lipid-rich cells in the dermis and epidermis. An exemplary range for cooling the lipid-rich cells not warmed or otherwise protected from heat generated by RF energy-conducting fibrous septae can be from about −10° C. to about 0° C.

Figure 4:
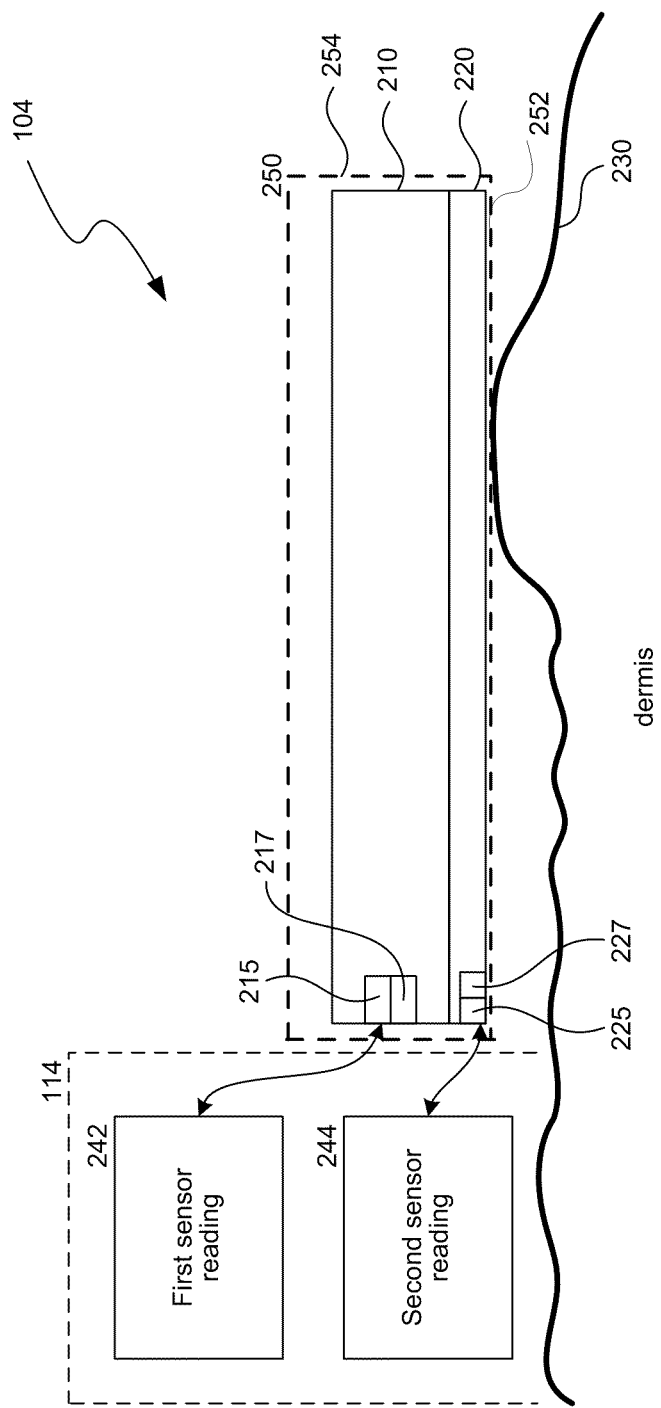
FIG. 4 is a partial cross-sectional view illustrating a combined modality treatment device suitable to be used in the system of FIG. 1 in accordance with embodiments of the disclosure.

FIG. 4 is a schematic, cross-sectional view illustrating a combined modality treatment device 104 for removing heat from bulging or herniating subcutaneous lipid-rich cells at or near the dermis—subcutaneous interface, or from adipose tissue separated or spaced apart from anchoring fibrous septae in the subcutaneous layer. The treatment device 104 can include a heat exchanging unit, such as a heat exchanging plate 210, and an interface layer 220. In one embodiment, the heat exchanging plate 210 is a thermally conductive aluminum plate that can be charged with RF current generated by the RF energy generating unit 107 (FIG. 1).

The heat exchanging plate 210 can contain a communication component 215 that communicates with the controller 114 to provide a first sensor reading 242 as described herein, and a sensor 217 that measures, e.g., temperature of the heat exchanging plate 210, heat flux across a surface of or plane within the heat exchanging plate 210 or RF current. The interface layer 220 can be a plate, a film, a covering, a sleeve or other suitable materials described herein and may serve as the patient protection device described herein. The interface layer 220 is located between the heat exchanging plate 210 and the skin 230 of a subject (not shown), such as the skin of a patient receiving treatment via the combined modality treatment device 104.

The interface layer 220 can also contain a similar communication component 225 that communicates with the controller 114 to provide a second sensor reading 244 and a sensor 227 that measures, e.g., the temperature of the interface layer 220, heat flux across a surface of or plane within the interface layer 220, RF current or contact pressure with the skin 230 of the patient. For example, one or both of the communication components 215, 225 can receive and transmit information from the controller 114, such as temperature and/or heat flux information as determined by one or both of the sensors 217, 227. The sensors 217, 227 are configured to measure a parameter of the interface without substantially impeding heat transfer between the heat exchanging plate 210 and the subject's skin 230. The treatment device 104 can also contain power components and other components described with respect to FIG. 1 and related applications.

In certain embodiments, the combined modality treatment device 104 can include a dielectric sleeve 250 for contacting the patient's skin 230 and for achieving a more uniform distribution of RF energy into the patient's underlying subcutaneous tissue. The sleeve 250 can include a first sleeve portion 252 and a second sleeve portion 254 extending from the first sleeve portion. The first sleeve portion 252 can contact and/or facilitate the contact of the combined modality treatment device 104 with the patient's skin 230, while the second sleeve portion 254 can be an isolation layer extending from the first sleeve portion 252. The second sleeve portion 254 can be constructed from latex, rubber, nylon, Kevlar®, or other substantially impermeable or semi-permeable material. The second sleeve portion 254 can prevent contact between the patient's skin 230 and the heat exchanging plates 210, among other things.

The surface of the first sleeve portion 252 can include a dielectric or variable resistance material providing an insulator between the RF conductive heat exchanging plate 210 and interface layer 220 and the patient's skin 230. For example, the material can include material coated or comprised of Teflon®, silicon nitride, polysilanes, polysilazanes, polyimides, Kapton and other polymers or dielectric materials well known in the art. The capacitive effect of the dielectric layer (e.g., the first sleeve portion 252) can be controlled, for example, through sleeve thickness, surface area the dielectric constant of the material and the frequency of the RF energy generated. In some embodiments, the first sleeve portion 252 extends beyond the edges of the RF conductive heat exchanging plate 210 and/or other electrodes such that the RF current is required to flow through the dielectric material of the first sleeve portion 252. Further details regarding a suitable sleeve may be found in U.S. Patent Publication No. 2008/0077201.

In other embodiments, the combined modality treatment device 104 can include a belt that assists in forming a contact between the treatment device 104 (such as via an interface layer 220) and the patient's skin 230. For example, the treatment device 104 can include retention devices (not shown) coupled to a frame. The retention devices may be rotatably connected to the frame by a plurality of coupling elements that can be, for example, pins, ball joints, bearings, or other type of rotatable joints. Alternatively, the retention devices can be rigidly affixed to the end portions of heat exchanging element housings. Further details regarding a suitable belt device may be found in U.S. Patent Publication No. 2008/0077211.

In further embodiments, the combined modality treatment device 104 can include a vacuum (not shown) that assists in forming a contact between the treatment device 104 (such as via the interface layer 220 or dielectric sleeve 250) and the patient's skin 230. For example, the treatment device 104 can provide mechanical energy to a treatment region. Imparting mechanical vibratory energy to the patient's tissue by repeatedly applying and releasing a vacuum to the subject's tissue, for instance, creates a massage action during treatment. Further details regarding a vacuum type device may be found in U.S. Patent Application Publication No. 2008/0287839.

In current practice, non-invasive cryotherapy applications used for body contouring applications are used to uniformly treat adipose tissue in a subject's target region. In body regions that are characterized by non-uniform distribution of adipose tissue due to bulging or herniating lipid-rich lobules at or near the dermis—subcutaneous interface, or other subcutaneous regions lacking sufficient connective tissue, cooling therapy alone may not result in selective disruption of the adipose tissue responsible for visible irregularities in the surface of the skin (e.g., cellulite). Also in current practice, thermal therapy has been used to disrupt and alter the three dimensional structure of collagen in subcutaneous tissue by applying thermal energy at frequencies sufficient to heat the fibrous septae to temperatures exceeding a collagen denaturation temperature. However, such thermal therapies do not address uneven distribution of adipose tissue or penetration of lipid-rich lobules into the dermis.

In contrast to the known practices in the art, the systems, devices and methods disclosed herein facilitate selective disruption of lipid-rich lobules in a manner that reduces irregularities in a surface of a subject's skin. For example, the systems, devices and methods disclosed herein use capacitively or conductively coupled RF energy in a manner to protectively and selectively heat fibrous septae and closely associated lipid-rich cells (e.g., closely packed adipose tissue) such that the resistively-generated heat in this tissue is sufficient to prevent cooling of this tissue to a disruption temperature (e.g., below 10° C.-15° C.). Accordingly the lipid rich lobules at or near the dermis—subcutaneous interface, or other subcutaneous regions lacking sufficient connective tissue, can be selectively disrupted during the treatment process such that treatment results in consistent and effective reduction in skin irregularities and cellulite.

C. Combined Modality Treatment Methods

The system 100 can be used to perform several combined modality treatment methods. Although specific examples of methods are described herein, one skilled in the art is capable of identifying other methods that the system could perform. Moreover, the methods described herein can be altered in various ways. As examples, the order of illustrated logic may be rearranged, sub-stages may be performed in parallel, illustrated logic may be omitted, other logic may be included, etc.

Figure 5:
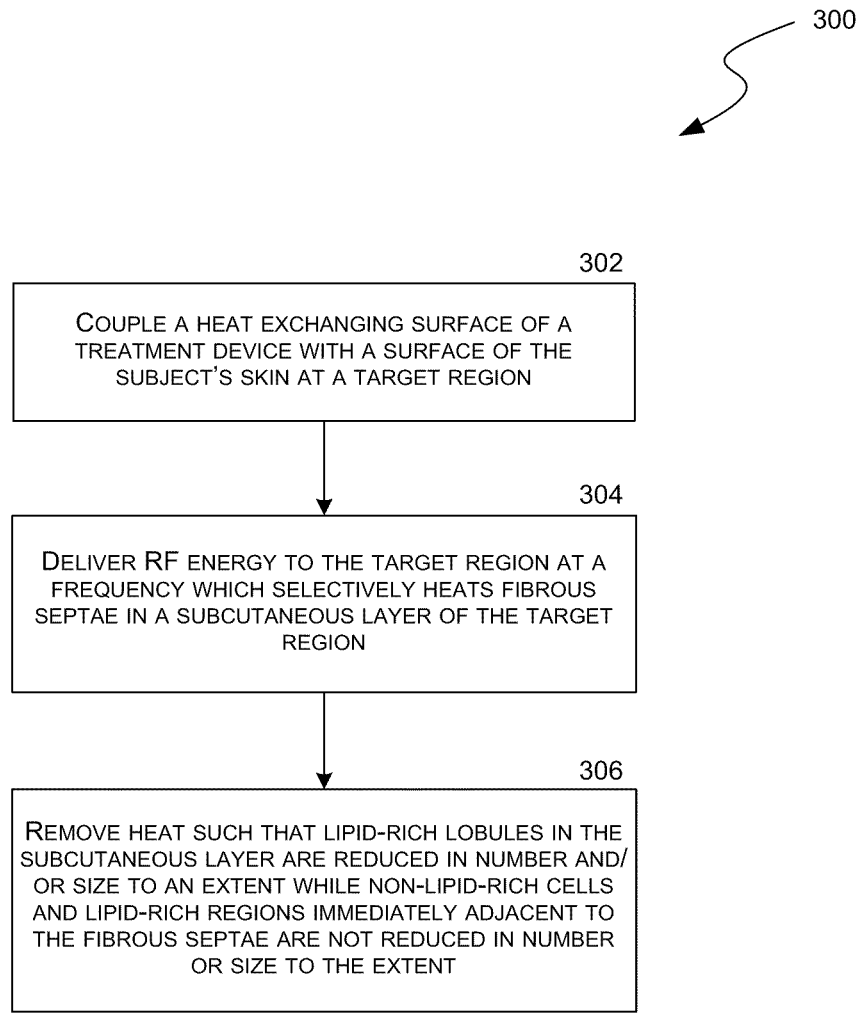
FIG. 5 is a flow diagram illustrating a method for reducing irregularities in a surface of a subject's skin resulting from an uneven distribution of adipose tissue in the subcutaneous layer in accordance with an embodiment of the disclosure.

FIG. 5 is a flow diagram illustrating a method 300 for reducing irregularities in a surface of a subject's skin resulting from an uneven distribution of adipose tissue in the subcutaneous layer in accordance with embodiments of the disclosure. Even though the method 300 is described below with reference to the combined modality treatment system 100 of FIG. 1 and the combined modality treatment device 104 of FIG. 4, the method 300 may also be applied in other treatment systems with additional or different hardware and/or software components.

As shown in FIG. 5, an early stage of the method 300 can include coupling a heat exchanging surface of a treatment device with the surface of the subject's skin at a target region (block 302). In one embodiment, the heat exchanging surface can be a surface of a heat exchanging plate. In another embodiment, the heat exchanging surface can be the surface of an interface layer or a dielectric layer. Coupling of the heat exchange surface to the surface of the skin can be facilitated by using restraining means, such as a belt or strap. In other embodiments, a vacuum or suction force can be used to positively couple the patient's skin at the target region to the heat exchange surface. Additionally, coupling the heat exchanging device to the subject's skin can also include providing a cryoprotectant to the patient's skin as is described in commonly assigned U.S. Patent Publication No. 2007/0255362.

The method 300 can also include delivering radiofrequency (RF) energy to the target region at a frequency sufficient selectively to heat fibrous septae in a subcutaneous layer of the target region (block 304). In some embodiments, the RF energy may be monopolar while in other embodiments it may be bipolar. In some embodiments, the RF energy may be capacitively coupled while in other embodiments it may be conductively coupled. In one embodiment, the RF energy can be delivered at a frequency of about 0.3 MHz to about 6 MHz. In other embodiments, the RF energy can be delivered at a frequency of between about 0.3 MHz to about 100 MHz or higher while in still other embodiments such RF energy can be delivered at a frequency of between about 0.3 MHz to about 40 MHz. In some embodiments, selective heating of the fibrous septae can include heating the fibrous septae to a final temperature less than a fibrous septae denaturation temperature (e.g., about 60° C.). For example, selective heating of the fibrous septae can include heating the fibrous septae to a temperature that does not denature fibrous septae. The fibrous septae can provide a path for preferentially conducting RF current through the subcutaneous layer. As the natural resistance of fibrous septae to the movement of charged ions and molecules in the subcutaneous tissue causes the fibrous septae to generate heat. One of ordinary skill in the art will recognize that the RF power (e.g., measured in watts) delivered to the target region, to achieve a desired fibrous septae temperature range, will be proportional to the surface area of the target region treated among other factors. In some aspects, selectively heating the fibrous septae includes preventing the fibrous septae and the lipid-rich regions adjacent to the fibrous septae from cooling to a temperature below approximately 10° C.-15° C.

At block 306, the method 300 includes removing heat such that lipid-rich cells in the subcutaneous layer are reduced in number and/or size to an extent while non-lipid-rich cells and lipid-rich regions adjacent to the fibrous septae are not reduced in number or size to the extent. For example, removing heat from the subcutaneous layer in the target region can include cooling the lipid-rich tissue to a temperature below 10° C. such that the lipid-rich lobules, and the adipose cells are disrupted.

Delivering the RF energy to the target region and removing heat from the subcutaneous layer in the target region may occur simultaneously. For example, the treatment method 300 may include a single stage or multiple stages of delivering RF energy with each such stage occurring simultaneously with a single stage or multiple stages of removing heat from the lipid-rich cells in the target region.

Alternatively, delivering the RF energy to the target region and removing heat from the subcutaneous layer in the target region may occur sequentially. For example, the method 300 may consist of a single stage of delivering RF energy that ceases prior to a single stage to remove heat from the lipid-rich cells in the target region. Additionally, such sequential application of the aforementioned stages may occur multiple times so that multiple non-overlapping stages of RF energy delivery and heat removal occur.

Another way that method 300 may be accomplished is by periodically or intermittently delivering RF energy to the target region of the subject simultaneously with removing heat. For example, method 300 may comprise a single stage of removing heat from the lipid-rich cells in the target region during which stage RF energy is delivered in multiple stages in a regular, periodic fashion or in a less regular, intermittent fashion, Alternatively, method 300 may include a single stage of delivering RF energy to the target region during which stage removing heat from the target region is accomplished in multiple stages in a regular, periodic fashion or in a less regular, intermittent fashion.

The duration of delivering the RF energy to the target region according to the embodiments described herein for reducing irregularities in a surface of skin of a subject resulting from an uneven distribution of adipose tissue in a subcutaneous layer of that subject, including in accordance with the method 300, may vary depending on the location of the target region, the degree of warming required, the power setting, whether the RF energy is capacitively or conductively coupled, the parameters of the stage of removing heat to reduce the number and/or size of the lipid-rich cells in the subcutaneous layer, and other parameters.

Such a duration may be calculated and described in terms of a single application of RF energy or cumulatively as summed over the course of more than one application of RF energy. For example, a single application of RF energy as described herein may range in duration from a second or less to several hours or more; e.g., the same or about the same duration as the duration of the stage of removing heat from the lipid-rich cells in the target region as described for example in U.S. Pat. No. 7,367,341, particularly when the RF energy is applied commensurately with the stage of removing heat. A duration of a period of application of RF energy in such an embodiment may, e.g., be between about 1 minute and about 2 hours, between about 1 minute and about 1 hour, between about 1 minute and about 50 minutes, or between about 1 minute and about 40 minutes, or between about 1 minute and about 30 minutes, or between about 1 minute and about 20 minutes. Still another embodiment results in a single application of RF energy of between about 5 minutes and about 15 minutes.

Applying RF energy in multiple stages as described herein, whether in periodic or intermittent fashion, for example, may also range cumulatively over those multiple stages in duration from a second or less to several hours or more. A cumulative duration of multiple stages of RF energy application in such embodiments may, e.g., be between about 1 minute and about 1 hour, or between about 1 minute and about 50 minutes, or between about 1 minute and about 40 minutes, or between about 1 minute and about 30 minutes, or between about 1 minute and about 20 minutes. Still another embodiment results in a cumulative duration of multiple stages of RF energy application of between about 5 minutes and about 15 minutes.

D. Suitable Computing Environments

Figure 6:
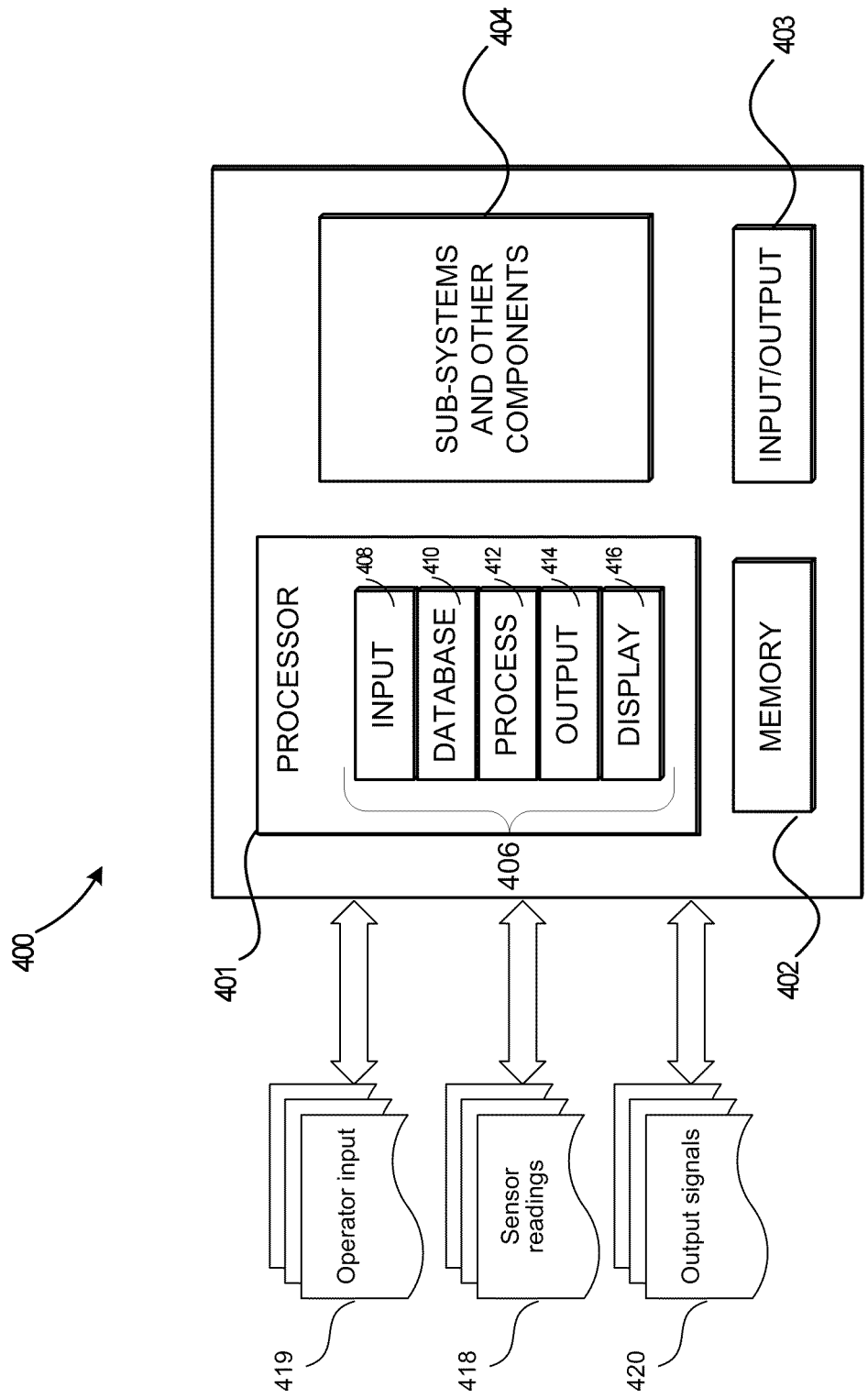
FIG. 6 is a schematic block diagram illustrating computing system software modules and subcomponents of a computing device suitable to be used in the system of FIG. 1 in accordance with an embodiment of the disclosure.

FIG. 6 is a schematic block diagram illustrating subcomponents of a computing device 400 in accordance with an embodiment of the disclosure. The computing device 400 can include a processor 401, a memory 402 (e.g., SRAM, DRAM, flash, or other memory devices), input/output devices 403, and/or subsystems and other components 404. The computing device 400 can perform any of a wide variety of computing processing, storage, sensing, imaging, and/or other functions. Components of the computing device 400 may be housed in a single unit or distributed over multiple, interconnected units (e.g., though a communications network). The components of the computing device 400 can accordingly include local and/or remote memory storage devices and any of a wide variety of computer-readable media.

As illustrated in FIG. 6, the processor 401 can include a plurality of functional modules 406, such as software modules, for execution by the processor 401. The various implementations of source code (i.e., in a conventional programming language) can be stored on a computer-readable storage medium or can be embodied on a transmission medium in a carrier wave. The modules 406 of the processor can include an input module 408, a database module 410, a process module 412, an output module 414, and, optionally, a display module 416.

In operation, the input module 408 accepts an operator input 419 via the one or more input devices described above with respect to FIG. 1, and communicates the accepted information or selections to other components for further processing. The database module 410 organizes records, including patient records, treatment data sets, treatment profiles and operating records and other operator activities, and facilitates storing and retrieving of these records to and from a data storage device (e.g., internal memory 402, an external database, etc.). Any type of database organization can be utilized, including a flat file system, hierarchical database, relational database, distributed database, etc.

In the illustrated example, the process module 412 can generate control variables based on sensor readings 418 from sensors (e.g., the temperature measurement components 217 and 227 of FIG. 4) and/or other data sources, and the output module 414 can communicate operator input to external computing devices and control variables to the controller 114. The display module 416 can be configured to convert and transmit processing parameters, sensor readings 418, output signals 320, input data, treatment profiles and prescribed operational parameters through one or more connected display devices, such as a display screen, printer, speaker system, etc. A suitable display module 416 may include a video driver that enables the controller 114 to display the sensor readings 418 or other status of treatment progression on the output device 120 (FIG. 1).

In various embodiments, the processor 401 can be a standard central processing unit or a secure processor. Secure processors can be special-purpose processors (e.g., reduced instruction set processor) that can withstand sophisticated attacks that attempt to extract data or programming logic. The secure processors may not have debugging pins that enable an external debugger to monitor the secure processor's execution or registers. In other embodiments, the system may employ a secure field programmable gate array, a smartcard, or other secure devices.

The memory 402 can be standard memory, secure memory, or a combination of both memory types. By employing a secure processor and/or secure memory, the system can ensure that data and instructions are both highly secure and sensitive operations such as decryption are shielded from observation.

Suitable computing environments and other computing devices and user interfaces are described in commonly assigned U.S. Provisional Patent Application Ser. No. 61/100, 248, entitled "TREATMENT PLANNING SYSTEMS AND METHODS FOR BODY CONTOURING APPLICATIONS," filed on Sep. 25, 2008, which is incorporated herein in its entirety by reference.

E. Conclusion

Various embodiments of the technology are described above. It will be appreciated that details set forth above are provided to describe the embodiments in a manner sufficient to enable a person skilled in the relevant art to make and use the disclosed embodiments. Several of the details and advantages, however, may not be necessary to practice some embodiments. Additionally, some well-known structures or functions may not be shown or described in detail, so as to avoid unnecessarily obscuring the relevant description of the various embodiments. Although some embodiments may be within the scope of the claims, they may not be described in detail with respect to the Figures. Furthermore, features, structures, or characteristics of various embodiments may be combined in any suitable manner. Moreover, one skilled in the art will recognize that there are a number of other technologies that could be used to perform functions similar to those described above and so the claims should not be limited to the devices or routines described herein. While processes or blocks are presented in a given order, alternative embodiments may perform routines having stages, or employ systems having blocks, in a different order, and some processes or blocks may be deleted, moved, added, subdivided, combined, and/or modified. Each of these processes or blocks may be implemented in a variety of different ways. Also, while processes or blocks are at times shown as being performed in series, these processes or blocks may instead be performed in parallel, or may be performed at different times. The headings provided herein are for convenience only and do not interpret the scope or meaning of the claims.

The terminology used in the description is intended to be interpreted in its broadest reasonable manner, even though it is being used in conjunction with a detailed description of identified embodiments.

Unless the context clearly requires otherwise, throughout the description and the claims, the words "comprise," "comprising," and the like are to be construed in an inclusive sense as opposed to an exclusive or exhaustive sense; that is to say, in a sense of "including, but not limited to." Words using the singular or plural number also include the plural or singular number, respectively. When the claims use the word "or" in reference to a list of two or more items, that word covers all of the following interpretations of the word: any of the items in the list, all of the items in the list, and any combination of the items in the list.

Some of the functional units described herein have been labeled as modules, in order to more particularly emphasize their implementation independence. For example, modules may be implemented in software for execution by various types of processors. An identified module of executable code may, for instance, comprise one or more physical or logical blocks of computer instructions which may, for instance, be organized as an object, procedure, or function. The identified blocks of computer instructions need not be physically located together, but may comprise disparate instructions stored in different locations which, when joined logically together, comprise the module and achieve the stated purpose for the module.

A module may also be implemented as a hardware circuit comprising custom VLSI circuits or gate arrays, off-the-shelf semiconductors such as logic chips, transistors, or other discrete components. A Module may also be implemented in programmable hardware devices such as field programmable gate arrays, programmable array logic, programmable logic devices or the like.

A module of executable code may be a single instruction, or many instructions, and may even be distributed over several different code segments, among different programs, and across several memory devices. Similarly, operational data may be identified and illustrated herein within modules, and may be embodied in any suitable form and organized within any suitable type of data structure. The operational data may be collected as a single data set, or may be distributed over different locations including over different storage devices, and may exist, at least partially, merely as electronic signals on a system or network.

Any patents, applications and other references, including any that may be listed in accompanying filing papers, are incorporated herein by reference. Aspects of the described technology can be modified, if necessary, to employ the systems, functions, and concepts of the various references described above to provide yet further embodiments.

These and other changes can be made in light of the above Detailed Description. While the above description details certain embodiments and describes the best mode contemplated, no matter how detailed, various changes can be made. Implementation details may vary considerably, while still being encompassed by the technology disclosed herein. As noted above, particular terminology used when describing certain features or aspects of the technology should not be taken to imply that the terminology is being redefined herein to be restricted to any specific characteristics, features, or aspects of the technology with which that terminology is associated. In general, the terms used in the following claims should not be construed to limit the claims to the specific embodiments disclosed in the specification, unless the above Detailed Description section explicitly defines such terms. Accordingly, the actual scope of the claims encompasses not only the disclosed embodiments, but also all equivalents.

I claim:

1. A system for non-invasive, transdermal removal of heat from subcutaneous lipid-rich cells of a subject, comprising:
   a treatment unit in thermal communication with a fluid chamber, the fluid chamber being configured to house and provide a coolant;
   a radiofrequency (RF) energy generating unit for generating RF current;
   a treatment device in fluid communication with the treatment unit and in electrical communication with the RF energy generating unit; and
   a controller in communication with the treatment unit, the RF energy generating unit and the treatment device, wherein the controller has instructions for causing the treatment device to:
   couple RF energy to the subject selectively to heat connective tissue in a target region beneath an epidermis of the subject to a maximum temperature less than a collagen denaturation temperature; and
   reduce a temperature of the target region beneath the epidermis of the subject selectively to reduce the temperature of subcutaneous lipid-rich cells in the target region such that the subcutaneous lipid-rich cells are substantially affected while non-lipid rich cells in the epidermis and subcutaneous lipid-rich cells adjacent to the connective tissue are not substantially affected.

2. The system of claim 1 wherein the treatment device is configured to capacitively couple RF energy to the subject.

3. The system of claim 2 wherein the treatment device capacitively couples monopolar RF energy to the subject, and wherein the system further includes a return electrode positioned adjacent to the epidermis of the subject at a region separated from the target region.

4. The system of claim 1 wherein the treatment device is configured to conductively couple RF energy to the subject.

5. The system of claim 1 wherein the collagen denaturation temperature is approximately 60° C.

6. The system of claim 1 wherein the connective tissue is selectively heated to a maximum temperature between approximately 0° C. to approximately 10° C.

7. The system of claim 1 wherein the connective tissue selectively is heated to a maximum temperature such that subcutaneous lipid-rich cells adjacent to the connective tissue are not cooled to temperatures below approximately 10° C.-15° C., and such that subcutaneous lipid-rich cells remote from the connective tissue are cooled to a temperature approximately less than 10° C.

8. The system of claim 1 wherein the radiofrequency (RF) energy generating unit produces an RF current of approximately 0.3 MHz to approximately 40 MHz.

9. The system of claim 1 wherein the controller is configured to cause the treatment device to remove heat from the target region while delivering the RF energy to the target region.

10. The system of claim 1 wherein the treatment device is configured to deliver the RF energy at a frequency of about 0.3 MHz to about 40 MHz.

11. The system of claim 1 wherein the controller has instructions for causing the treatment device to deliver the RF energy to the target region while removing heat from the target region.

12. The system of claim 1 wherein the controller is configured to cause the treatment device to sequentially remove heat from the target region and deliver the RF energy to the target region.

13. A combined modality treatment system for selectively removing heat from subcutaneous lipid-rich cells in a target region of a subject having skin, comprising:
- a treatment unit in thermal communication with a fluid chamber, the fluid chamber being configured to house and provide a coolant;
- a radiofrequency (RF) energy source for generating RF current;
- a controller; and
- a treatment device having a heat exchanging plate coupled to the RF energy source and a thermoelectric cooling element in communication with the treatment unit;
- wherein the controller has instructions that cause the treatment device to—
  - capacitively couple radiofrequency (RF) energy to the skin of the subject selectively to heat fibrous septae in the target region to a final temperature less than a fibrous septae denaturation temperature; and
  - remove heat from the subcutaneous lipid-rich cells of the subject during a treatment process such that subcutaneous lipid-rich cells are substantially affected while non-lipid-rich cells and subcutaneous lipid-rich cells adjacent to the fibrous septae are not substantially affected.

14. The system of claim 13 wherein the heat exchanging plate is a thermally conductive aluminum plate that can be charged with RF current.

15. The system of claim 13 wherein the treatment device further comprises an interface layer positioned between the heat exchanging plate and the skin of the subject, the interface layer configured to form an RF energy and heat conducting interface with the skin.

16. The system of claim 15 wherein the treatment device further comprises a dielectric layer positioned between the heat exchanging plate and the skin of the subject, the dielectric layer configured to capacitively couple the RF energy from the heat exchanging plate to the skin of the patient.

17. The system of claim 16 wherein the dielectric layer provides a more uniform distribution of RF energy into the target region of the subject.

18. The system of claim 16 wherein the dielectric layer is a dielectric sleeve, the dielectric sleeve including a first sleeve portion and a second sleeve portion extending from the first sleeve portion, the first sleeve portion comprising variable resistance material as insulation between the RF conductive heat exchanging plate and the skin of the patient, and wherein the second sleeve portion is an electrical isolation layer extending from the first sleeve portion.

19. The system of claim 13 wherein the fibrous septae denaturation temperature is approximately 60° C.

20. The system of claim 13 wherein the fibrous septae are selectively heated to a final temperature between approximately 0° C. and approximately 60° C.

21. The system of claim 13 wherein the fibrous septae are selectively heated to a final temperature such that subcutaneous lipid-rich cells adjacent to the fibrous septae are not cooled to temperatures below approximately 10° C.-15° C., and such that subcutaneous lipid-rich cells remote from the fibrous septae are cooled to a temperature approximately less than 10° C.

22. The system of claim 13 wherein the treatment device is configured to deliver the RF energy at a frequency of about 0.3 MHz to about 40 MHz.

23. The system of claim 13 wherein the controller is configured to receive instructions to cause the treatment device to cool the lipid-rich cells to a temperature below about 10° C.

24. The system of claim 13 wherein the controller is configured to cause the cause the treatment device to deliver the RF energy while the treatment device cools the lipid-rich cells to a temperature below about 10°.

25. The system of claim 13 wherein the treatment device is configured to deliver ultrasound energy.

26. The system of claim 13 wherein the treatment device is configured to deliver microwave energy.

27. The system of claim 13 wherein the controller has instructions for causing the treatment device to deliver the RF energy to the target region while removing heat from the target region.

28. The system of claim 13, wherein the treatment device is configured to deliver the RF energy from the RF energy source to the skin of the subject and to remove heat from the subject via the heat exchanging plate.

29. The system of claim 13 wherein the treatment device is configured to deliver one or more of optical energy, acoustic energy, and microwave to the subject's skin.

30. The system of claim 13 wherein the controller is configured to sequentially remove heat from the target region and deliver the RF energy to the target region.

* * * * *